United States Patent [19]

Svendsen

[11] 4,428,874
[45] Jan. 31, 1984

[54] TRIPEPTIDE DERIVATIVES

[75] Inventor: Lars G. Svendsen, Reinach, Switzerland

[73] Assignee: Pentapharm A.G., Basel, Switzerland

[21] Appl. No.: 247,621

[22] Filed: Mar. 25, 1981

[51] Int. Cl.³ .................... C07C 103/52; C12Q 1/36
[52] U.S. Cl. .................... 260/112.5 R; 435/24
[58] Field of Search .................... 260/112.5 R; 435/24

[56] References Cited

U.S. PATENT DOCUMENTS

| | | | |
|---|---|---|---|
| 3,886,136 | 5/1975 | Claeson et al. | 260/112.5 R |
| 4,061,625 | 12/1977 | Af Ekenstam et al. | 260/112.5 R |
| 4,308,201 | 12/1981 | Fujii et al. | 260/112.5 R |

*Primary Examiner*—Delbert R. Phillips
*Attorney, Agent, or Firm*—Pennie & Edmonds

[57] ABSTRACT

Tripeptide derivatives which are useful as substrates for assaying proteolytic enzymes. The said derivatives are compounds of formula

H—D—X—Y—Z—R wherein X represents a cyclohexylglycyl, cyclohexylalanyl, p-hydroxycyclohexylalanyl, phenylglycyl, phenylalanyl, tyrosyl, leucyl, isoleucyl, norleucyl, valyl, norvalyl, α-aminobutyryl, alanyl, prolyl or pipecolinoyl group, Y represents a cyclohexylglycyl, cyclohexylalanyl, p-hydroxycyclohexylalanyl, phenylglycyl, phenylalanyl or tyrosyl group and, if the meaning of X is limited to cyclohexylglycyl, cyclohexylalanyl, p-hydroxycyclohexylalanyl, phenylglycyl, phenylalanyl or tyrosyl, additionally a leucyl, isoleucyl, norleucyl, valyl, norvalyl, α-aminobutyryl, alanyl, prolyl or pipecolinoyl group, Z represents an arginyl or lysyl group and R represents a chromogenic group which can be split off by enzymatic hydrolysis and which is capable of forming a colored or fluorescent compound. The tripeptide derivatives are preferably used in the form of their salts with acids.

6 Claims, No Drawings

TRIPEPTIDE DERIVATIVES

The present invention relates to novel tripeptide derivatives which are useful as substrates for the quantitative assay of proteolytic enzymes, particularly enzymes of the enzyme class E.C. 3.4.21., e.g. organ or glandular kallikrein, thrombin and plasmin.

So-called organ kallikrein or glandular kallikrein is produced by various organs and glands, e.g. the pancreatic gland, salivary gland, kidney, mucosa of the digestive tract, etc., and secreted in the form of a proenzyme or in an active form. These organ or glandular kallikreins differ chemically and physiologically from plasma kallikrein. In certain pathological conditions the organ kallikrein secretion level drops below or rises above the normal value. Thus, for example, the kallikrein secretion in urine drops substantially below the normal value in patients suffering from kidney diseases. In patients suffering from cirrhosis of the kidney the kallikrein secretion is almost completely suppressed. In patients suffering from essential hypertension the kallikrein secretion in 24 hour-urine is significantly reduced, as an average by 50% of the normal value (cf. e.g. H. S. Margolius in "Chemistry and Biology of the Kallikrein-Kinin System in Health and Disease", 1974, p. 399–409). Therefore, it is important to have at one's disposal simple methods for a quick quantitative assay of organ kallikrein. It is known, e.g., to assay urine kallikrein by esterolysis of certain arginine esters, e.g. tosyl-arginine methyl ester (TAME). In an improved esterolytic method tosyl-arginine methyl ester marked with tritium is used and the radioactivity of the methanol released by esterolysis is measured. These esterolytic methods suffer from the disadvantage that they are unbiological insofar as the kallikreins are proteolytic enzymes which split natural peptide chains amidolytically but not esterolytically. Furthermore, ester substrates have the disadvantage that they are split by numerous other enzymes, i.e. are split unspecifically by kallikrein. The method using TAME marked with tritium is complex insofar as, prior to the measurement of the radioactivity of the methanol marked with tritium, the methanol has to be extracted from the esterolysis mixture with a liquid which is not miscible with water since otherwise the residual TAME marked with tritium still present in the esterolysis mixture would inhibit the measurement.

In the unexamined prepublished German patent application OS No. 25 27 932 substrates having the formula R$^1$—Pro—X—Arg—NH—R$^2$ are described in which R$^1$ represents a blocking group, —NH—R$^2$ represents a chromogenic group and X represents a phenylalanyl, β-cyclohexylalanyl, phenylglycyl or tyrosyl group. These substrates are split very easily by plasma kallikrein and yield a colored split product R$^2$—NH$_2$ the quantity of which can be measured by photometric, spectrophotometric or fluorescence photometric methods. An attempt was made to also use these substrates for assaying organ or glandular kallikreins. However, it was surprisingly found that the said substrates are not sensitive to organ or glandular kallikrein, i.e. are not split or only split to a small extent by the latter.

In the unexamined prepublished German patent application No. OS 26 29 067 tripeptide derivatives are described which are useful as substrates for assaying certain proteolytic enzymes, e.g. glandular or organ kallikreins and plasmin. Two examples are mentioned there, viz. H-D-valyl-leucyl-arginyl-p-nitroanilide dihydrochloride and H-D-valyl-leucyl-lysyl-p-nitroanilide dihydrochloride. The first tripeptide derivative is a substrate for glandular kallikrein, whereas the second tripeptide derivative is a substrate for plasmin. The two compounds are split by the said enzymes and yield p-nitroaniline the quantity of which can be measured photometrically or spectrophotometrically. However, the susceptibility of H-D-valyl-leucyl-arginyl-p-nitroanilide dihydrochloride just about reaches the threshold value required for the accurate assaying of urine kallikrein in unconcentrated urine. If, however, the said amide substrate is used in concentrated urine, the photometric measurement of p-nitroaniline is strongly impaired by the intrinsic color of urine.

The first two amino acids in the tripeptide chain of the two tripeptide derivatives mentioned in the above said German patent application carry hydrophobic isopropyl groups in the α- or β-position. It was attempted to replace the isopropyl groups by aromatic groups, e.g. phenyl groups, while maintaining the basic structure of the dipeptide chain, in order to increase the hydrophobicity and, consequently, the susceptibility to glandular kallikrein. However, this attempt failed. The tripeptide substrates obtained by the introduction of aromatic groups are not split at all or split at most to a very small extent by glandular kallikrein. However, these tripeptide substrates carrying aromatic groups have a surprisingly high susceptibility to plasmin. Moreover, it was found, unexpectedly, that hydrogenation of the aromatic radicals in the said tripeptide plasmin substrates leads to new tripeptide substrates which have a surprisingly high susceptibility to organ or glandular kallikreins. It had been believed that in the building up of tripeptide chains only naturally occurring amino acids could be used in order to obtain substrates which would be split by proteolytic enzymes. Therefore, it was surprising to find that, by using amino acids which contain cyclohexyl radicals and which do not occur in nature, one could obtain chromogenic substrates which are easily split by organ or glandular kallikreins and other proteolytic enzymes, e.g. plasma kallikrein.

The invention relates to new chromogenic substrates which have a high susceptibility to certain proteolytic enzymes, particularly enzymes of the enzyme class E.C. 3.4.21., e.g. organ or glandular kallikreins, plasmin and thrombin and, therefore, are useful as substrates for the quantitative assay of these enzymes. These substrates are tripeptide derivatives of formula:

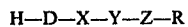

H—D—X—Y—Z—R        1 wherein
X represents a cyclohexylglycyl, cyclohexylalanyl, p-hydroxycyclohexylalanyl, phenylglycyl, phenylalanyl, tyrosyl, leucyl, isoleucyl, norleucyl, valyl, norvalyl, α-aminobutyryl, alanyl, prolyl or pipecolinoyl group,
Y represents a cyclohexylglycyl, cyclohexylalanyl, p-hydroxycyclohexylalanyl, phenylglycyl, phenylalanyl, or tyrosyl group, and, if the meaning of X is limited to cyclohexylglycyl, cyclohexylalanyl, p-hydroxycyclohexylalanyl, phenylglycyl, phenylalanyl or tyrosyl, additionally a leucyl, isoleucyl, norleucyl, valyl, norvalyl, α-aminobutyryl, alanyl, prolyl or pipecolinoyl group,
Z represents an arginyl or lysyl group, and R represents a chromogenic group which is removable by enzymatic hydrolysis and capable of forming a colored or fluorescent compound R—NH$_2$.

The chromogenic group represented by R in formula I can be, e.g., a p-nitrophenylamino, 2-naphthylamino, 4-methoxy-2-naphthylamino, 4-methyl-coumaryl-(7)-amino, 1,3-di(methoxycarbonyl)-phenyl-(5)-amino, quinonyl, or nitroquinonyl group.

The tripeptide derivatives of formula I are difficultly soluble in aqueous media and, therefore, are preferably used in the form of their salts with acids, in particular their salts with mineral acids, e.g. HCl, HBr, H$_2$SO$_4$, H$_3$PO$_4$, etc., or organic acids, e.g. formic acid, acetic acid, propionic acid, trimethylacetic acid, methoxyacetic acid, halogenated acetic acids such as trichloro- or trifluoroacetic acid, aminoacetic acid, lactic acid, oxalic acid, malonic acid, citric acid, benzoic acid, aromatic acids substituted in the nucleus such as toluic acids, chloro- or bromobenzoic acids, methoxybenzoic acids and aminobenzoic acids, phthalic acid, etc. The nature of the acid is not critical since the acid does not participate in the reaction between the substrates and the enzymes.

The substrates of formula I and their salts with acids are split hydrolytically by the action of certain proteolytic enzymes, particularly enzymes of the enzyme class 3.4.21. (cf. "Enzyme Nomenclature", Elsevier Scientific Publishing Company, Amsterdam 1973, p. 238 ff), e.g. organ and glandular kallikreins, plasmin and thrombin, and as a result a colored or fluorescent split product of formula R—NH$_2$ is formed the quantity of which can be measured by photometric, spectrophotometric, fluorescence spectrophotometric or electrochemical methods. Therefore, the new substrates are useful for the quantitative assaying of proteolytic enzymes, in particular enzymes of the enzyme class E.C. 3.4.21., which split natural peptide chains on the carboxyl side of arginine as well as lysine, e.g. organ or glandular kallikreins, plasmin, plasma kallikrein, thrombin as well as their inhibitors and proenzymes, and also other factors which participate in the formation or inhibition of the said enzymes.

A preferred group of tripeptide derivatives comprises compounds of formula I wherein (a)
X represents a cyclohexylglycyl, cyclohexylalanyl or cyclohexyltyrosyl group and
Y represents an alanyl, α-aminobutyryl, valyl, norvalyl, leucyl, norleucyl, isoleucyl, prolyl or pipecolinoyl group, or (b)
Y represents a phenylalanyl, phenylglycyl or tyrosyl group and
X represents a cyclohexylglycyl, cyclohexylalanyl, cyclohexyltyrosyl, phenylalanyl or phenylglycyl group, or (c)
Y represents a cyclohexylglycyl, cyclohexylalanyl, cyclohexyltyrosyl, phenylglycyl or tyrosyl group and
X represents an alanyl, α-aminobutyryl, valyl, norvalyl, leucyl, norleucyl, isoleucyl or prolyl group, or (d)
X represents a phenylalanyl, phenylglycyl or cyclohexylglycyl group and
Y represents a cyclohexylalanyl, cyclohexylglycyl or cyclohexyltyrosyl group.

The tripeptide derivatives described in the following working Examples 3, 5, 7, 9, 12, 13, 14, 15, 16, 19, 23, 24, 34, 36, 37, 38, 39, 40, 41, 65, 71, 72 and 73 are useful in particular as substrates for assaying urine kallikrein.

For assaying kallikrein in human sputum the tripeptide derivatives described in the following working Examples 1, 3, 5, 7, 9, 12, 13, 15, 16, 23, 27, 34, 36, 37, 38, 39, 40, 41, 53, 54, 55, 56, 57, 58, 65, 67, 68, 69, 70, 71, 72, 73, 75, 76 and 77 can be used.

The tripeptide derivatives described in the following working Examples 1, 2, 4, 6, 8, 10, 16, 17, 18, 19, 23, 29, 32, 33, 35, 36, 37, 39, 41, 42, 43, 44, 45, 46, 47, 51, 57, 63, 64, 67, 68, 71, 73 and 74 constitute a group of substrates which can be used for assaying plasmin.

The tripeptide derivatives described in the following working Examples 19, 23, 27, 28, 48, 49, 51, 52, 56, 57, 58, 65, 66, 68, 69, 70, 75, 76 and 77 are very sensitive substrates for assaying thrombin.

The invention also relates to a method for the quantitative assay of proteolytic enzymes, in particular enzymes of the enzyme class E.C. 3.4.21., which split natural peptide chains on the carboxyl side of arginine as well as lysine, e.g. organ or glandular kallikreins, plasmin and thrombin. The method according to the invention comprises reacting materials which contain the above mentioned enzymes or in which the latter are formed or consumed with a tripeptide derivative of formula I, and measuring the quantity of the colored or fluorescent split product R—NH$_2$ formed by the hydrolytic action of the enzyme on the tripeptide derivative by photometric, spectrophotometric, fluorescence spectrophotometric or electrochemical methods. The method of the invention allows, e.g., the enzyme content of enzyme preparations or the enzyme level in human and mammal body fluids, e.g. urine, pancreatic juice, intestinal mucosa, milk gland secretion, sweat gland secretion, sputum and blood, to be assayed. The method of the invention is useful in particular for quantitatively assaying organ or glandular kallikreins in the above mentioned body fluids and plasma kallikrein. By means of this method free organ kallikreins and mucosa kallikreins as well as kallikreins formed from prekallikreins and, furthermore, physiological or non-physiological inhibitors of kallikreins and physiological or non-physiological activators of prekallikreins can be assayed.

The tripeptide derivatives of formula I can be prepared according to the methods described hereinafter:

(1) The chromogenic group R is attached to the carboxyl group of the C-terminal arginine or lysine, whereby the α-amino group is protected by a protective group, e.g. a carbobenzoxy or tert.-butoxycarbonyl group, the δ-guanidyl group, in the case of arginine, is protected by protonation, e.g. with HCl, nitration or tosylation, and the ε-amino group, in the case of lysine, is protected by a carbobenzoxy group, or a p-methyl-, p-methoxy- or p-chlorobenzyloxycarbonyl group, or a tert.-butoxycarbonyl group. The C-terminal R—NH— group also serves as a protective group during the stepwise synthesis of the peptide chain. The other protective groups can be removed selectively, as required, in order to attach the further amino acid derivatives until the desired peptide chain is completely synthesized. Eventually, the remaining protective groups are completely split off without the R—NH— group being affected (cf. e.g. Miklos Bodansky et al., "Peptide Synthesis", Interscience Publishers, 1966, p. 163–165).

(2) First the peptide chain is synthesized (according to Bodansky et al., loc.cit.) whereby, however, the C-terminal carboxyl group of arginine or lysine is protected by a usual ester group, e.g. a methoxy, ethoxy or benzyloxy group, in the case of arginine, or a tert.-butoxy group, in the case of lysine. The ester groups can be removed by alkaline hydrolysis, except the tert.-butoxy group which has to be split off selectively by means of trifluoroacetic acid. If the δ-guanidyl group of arginine is protonated, the said ester group is removed enzymatically by means of trypsin, no racemization taking place. Then, the chromogenic group R—NH— is attached. If the δ-guanidino group of arginine is protected by a nitro or tosyl group, or the ε-amino group of lysine is protected by a carbobenzoxy or tert.-butoxy group, and the N-terminal α-amino group of the tripeptide derivative is protected by a carbobenzoxy group or a p-methyl, p-methoxy or p-chlorobenzyloxycarbonyl group or a tert.-butoxy group, all protective groups are removed simultaneously. The removal can be carried out by treating the protected tripeptide derivative with anhydrous HF at room temperature, all the above mentioned protective groups of the amino and δ-guanidino groups being thus removed. The removal can also be carried out by treatment with 2 N HBr in glacial acetic acid at room temperature if the protected tripeptide derivative contains no protective nitro or tosyl group.

The preparation of the tripeptide derivatives of the invention is described in detail in the following working Examples.

The analyses of eluates and products obtained according to the Examples were performed by thin layer chromatography using glass plates coated with silica gel (Merck, F 254). The thin layer chromatograms were developed by the following solvent systems:
A: chloroform/methanol (9:1)
B: n-propanol/ethyl acetate/water (7:1:2)
C: n-butanol/acetic acid/water (3:1:1).
The following abbreviations are used:
AcOH=acetic acid
Ala=alanine
Arg=arginine
BOC=tert.-butoxycarbonyl
But=α-aminobutyric acid
Cbo=carbobenzoxy
CHA=cyclohexylalanine
CHG=cyclohexylglycine
CHT=cyclohexyltyrosine=p-hydroxycyclohexylalanine
DMF=dimethylformamide
DPA=1,3-di(methoxycarbonyl)-phenyl-(5-amide
TLC=thin layer chromatography
Et$_3$N=triethylamine
HMPTA=phosphoric acid N,N,N',N',N'',N''-hexamethyltriamide
Ile=isoleucine
Leu=leucine
SS=solvent system(s)
Lys=lysine
MCA=4-methyl-coumaryl-(7)-amide
MeOH=methanol
4-MeO-2-NA=4-methoxy-2-naphthylamide
Nleu=norleucine
Nval=norvaline
OpNP=p-nitrophenoxy
Phe=phenylalanine
Ph'Gly=phenylglycine
Pip=pipecolinic acid
pNA=p-nitroanilide
Pro=proline
THF=tetrahydrofuran
Tyr=tyrosine
Val=valine
If not otherwise stated, the amino acids in the peptide chains have the L-form.

EXAMPLE 1

H-D-CHG-CHA-Arg-pNA.2HBr

1a. Cbo-Arg-pNA.HCl

In a 250 ml three-necked flask 16.0 g (47.0 mmoles) of Cbo-Arg-OH.HCl, which had been dried in vacuo over P$_2$O$_5$, were dissolved in 90 ml of absolute HMPTA at 20° C., while keeping the atmosphere in the flask moisture-free. To the resulting solution there was added at room temperature first a solution of 4.74 g (47.0 mmoles) of Et$_3$N in 10 ml of HMPTA and then portionwise 16.4 g (100 mmoles) of p-nitrophenyl isocyanate (100% excess). After a reaction time of 24 hours at 20° C. the major portion of HMPTA was removed by distillation in vacuo. The residue was extracted several times with 30% AcOH. The residue was discarded. The combined acetic acid extracts were further purified by passing them through a column of "Sephadex G-15" (Trade Mark) equilibrated with 30% AcOH and eluted with 30% AcOH. The fraction of the AcOH eluate which was split by treatment with trypsin with liberation of p-nitroaniline was freeze-dried. There were thus obtained 12.6 g of an amorphous powder which was homogenous in SS C as shown by TLC. Elementary analysis and calculation from the empirical formula C$_{20}$H$_{25}$N$_6$O$_5$Cl gave the following values (the values from the empirical formula are put within brackets): C=51.29% (51.67%), H=5.48% (5.42%), N=17.92% (18.08%), Cl=7.50% (7.63%).

1b. 2HBr.H-Arg-pNA 4.65 g (10 mmoles) of compound 1a were treated, while stirring, with 40 ml of 2 N HBr in glacial acetic acid for 45 min. at 20° C. in the absence of moisture. The amino acid derivative dissolved with CO$_2$ evolution. The reaction solution was added dropwise with vigorous stirring to 250 ml of absolute ether. This resulted in the precipitation of 2HBr.H-Arg-pNA. The ethereal phase was sucked off, whereupon the solid phase was washed 4 times with portions of 100 ml of absolute ether in order to remove benzyl bromide which had formed as a byproduct as well as excess HBr and AcOH. The residue was dissolved in 50 ml of methanol, the pH was adjusted to 4.5 by the addition of Et$_3$N, and the solution was concentrated to dryness in vacuo at 30° C. The resulting product was dissolved in 75 ml of MeOH and passed through a column of "Sephadex LH-20" (crosslinked dextran gel) equilibrated with MeOH. From a fraction of the eluate there were obtained 4.18 g (91.6% of the theory) of amorphous compound 1b which was homogeneous in SS C as shown by TLC. Elementary analysis and calculation from the empirical formula C$_{12}$H$_{20}$N$_6$O$_3$Br$_2$ gave the following values: C=31.15% (31.60%), H=4.35% (4.42%), N=18.84% (18.43%) and Br=34.81% (35.03%).

1c. Cbo-CHA-Arg-pNa.HBr 4.56 g (10 mmoles) of compound 1b were dissolved in 30 ml of freshly distilled DMF, and the solution was cooled to −10° C. 1.40 ml (10 mmoles) of Et$_3$N were added to the solution, while stirring. The formed Et$_3$N.HBr was removed by filtration and washed with a small quantity of cold DMF. 4.69 g (11 mmoles) of Cbo-CHA-OpNP were added at −10° C. to the filtrate, and the reaction was allowed to proceed for 2-3 hours in the absence of moisture, whereby the temperature of the reaction solution gradually reached about 20° C. The solution was again cooled to −10° C., buffered with 0.70 ml (5 mmoles) of $Et_3N$ and allowed to react about 2 hours at −10° C. and about 3 hours at room temperature. This procedure was repeated with 0.70 ml of $Et_3N$, and after 16 hours the reaction solution was concentrated to dryness in vacuo at 50° C. The residue was dissolved in 75 ml of 50% AcOH and purified by gel filtration on a column of "Sephadex G-15" equilibrated with 50% AcOH. The main fraction of the AcOH eluate which was split by treatment with trypsin with liberation of p-nitroaniline was concentrated to dryness in vacuo at 40° C. The residue was dissolved in 150 ml of MeOH and again concentrated to dryness. The resulting residue was dried in a vacuum desiccator at 60° C. over $P_2O_5$ to obtain 5.85 g (88.3% of the theory) of the amorphous compound 1c which was homogeneous in SS C as shown by TLC. Elementary analysis and calculation from the empirical formula $C_{29}H_{40}N_7O_6Br$ gave the following values: C=52.28% (52.57%), H=6.16% (6.09%), N=15.09% (14.80%) and Br=11.85% (12.06%).

1d. $2HBr.H$-CHA-Arg-pNA 5.30 g (8 mmoles) of compound 1c were treated, while stirring, with 32 ml of 2 N HBr in glacial acetic acid for 40 min. at 20° C. The dipeptide derivative gradually dissolved with $CO_2$ evolution. The reaction solution was added dropwise with vigorous stirring to 250 ml of absolute ether. This resulted in the precipitation of $2HBr.H$-CHA-Arg-pNA. The ethereal phase was sucked off, whereupon the solid phase was washed 4 times with portions of 100 ml of absolute ether in order to remove benzyl bromide which had formed as a by-product as well as excess HBr and AcOH. The residue was dissolved in 50 ml of MeOH. The pH was adjusted to 4.5 by means of $Et_3N$, and the solution was concentrated to dryness in vacuo at 30° C. The resulting residue was dissolved in 50 ml of MeOH and purified on a column of "Sephadex LH-20" equilibrated with MeOH. The fraction of the MeOH eluate which was split by treatment with trypsin with liberation of p-nitroaniline was concentrated to dryness in vacuo at 30° C. The resulting residue was dried in a vacuum desiccator at 40° C. over $P_2O_5$ to obtain 4.48 g (91.9% of the theory) of amorphous compound 1d which was homogeneous in SS C. Elementary analysis and calculation from the empirical formula $C_{21}H_{35}N_7O_4Br$ gave the following values: C=41.80% (41.39%), H=5.86% (5.79%), N=16.31% (16.09%) and Br=25.85% (26.23%).

1e. Cbo-D-CHG-CHA-Arg-pNA.HBr 3.05 g (5 mmoles) of compound 1d were dissolved in 20 ml of freshly distilled DMF, and the solution was cooled to −10° C. 0.70 ml (5 mmoles) of $Et_3N$ were added to the solution, while stirring. The formed $Et_3N.HBr$ was removed by filtration and washed with a small quantity of cold DMF. 2.27 g (5.5 mmoles) of Cbo-D-CHG.OpNP were added at −10° C. to the filtrate, while stirring. The reaction mixture was allowed to react for 2-3 hours in the absence of moisture, whereby the temperature of the reaction solution gradually reached about 20° C. The solution was again cooled to −10° C., buffered with 0.35 ml (2.5 mmoles) of $Et_3N$ and allowed to react for about 2 hours at −10° C. and for a further 3 hours at room temperature. This procedure was repeated with 0.35 ml of $Et_3N$, and after 16 hours the reaction solution was concentrated to dryness in vacuo at 50° C. The residue was dissolved in 50 ml of 50% AcOH and purified by gel filtration on a column of "Sephadex G-15" equilibrated with 50% AcOH. The main fraction of the AcOH eluate which was split by treatment with trypsin with liberation of p-nitroaniline was concentrated to dryness in vacuo at 40° C. The residue was dissolved in 100 ml of MeOH, and the solution was again concentrated to dryness. The resulting residue was dried in a vacuum desiccator at 60° C. over $P_2O_5$ to obtain 3.24 g (80.8% of the theory) of the amorphous compound 1e which was homogeneous in SS C as shown by TLC. Elementary analysis and calculation from the empirical formula $C_{37}H_{53}N_8O_7Br$ gave the following values: C=55.72% (55.43%), H=6.73% (6.66%), N=14.25% (13.98%) and Br=9.86% (9.97%).

1f. $2HBr.H$-D-CHG-CHA-Arg-pNA 2.41 g (3 mmoles) of compound 1e were treated, while stirring, with 12 ml of 2 N HBr in glacial acetic acid for 40 minutes at 20° C. in the absence of humidity. The tripeptide derivative gradually dissolved with decarboxylation and $CO_2$ evolution. The reaction solution was added dropwise with vigorous stirring to 120 ml of absolute ether. This resulted in the precipitation of $2HBr.H$-D-CHG-CHA-Arg-pNA. The ethereal phase was sucked off through a filter rod, and then the solid phase was washed 4 times with portions of 50 ml of absolute ether. The resulting residue was dissolved in 40 ml of MeOH. The pH was adjusted to 4.5 by means of $Et_3N$, and the solution was concentrated to dryness in vacuo at 30° C. The residue was dissolved in 30 ml of MeOH and purified on a column of "Sephadex LH-20" equilibrated with MeOH. The fraction of the MeOH eluate which was split by treatment with trypsin with liberation of p-nitroaniline was concentrated to dryness in vacuo at 30° C. For a further purification the pre-purified residue was dissolved in 30 ml of 33% AcOH and purified by gel filtration on a column of "Sephadex G-15" equilibrated with 33% AcOH. The main fraction of the AcOH eluate which was split by treatment with trypsin with liberation of p-nitroaniline was concentrated to dryness in vacuo at 40° C. The resulting residue was dried in a vacuum desiccator at 40° C. over $P_2O_5$ to obtain 1.68 g (74.8% of the theory) of amorphous compound 1f which was homogeneous in SS C as shown by TLC. Elementary analysis and calculation from the empirical formula $C_{29}H_{48}N_8O_5Br_2$ gave the following values: C=46.18% (46.53%), H=6.55% (6.46%), N=15.18% (14.97%) and Br=21.12% (21.35%).

The amino acid analysis confirmed the presence of the expected amino acids in the correct proportions: Arg: 1.00-CHA: 0.96-D-CHG: 0.98.

EXAMPLE 2

$2HBr.H$-D-CHG-Phe-Lys-pNA

2a. BOC-Lys($\epsilon$-Cbo)-pNA 38.05 g (0.1 mole) of dried oil of BOC-Lys($\epsilon$-Cbo)-OH were dissolved in a 500 ml three-necked flask in 150 ml of absolute HMPTA at 20° C. in the absence of moisture. To the resulting solution there was added at room temperature first a solution of 10.12 g (0.1 mole) of $Et_3N$ in 25 ml of HMPTA and then portionwise 24.62 g (0.15 mole) of p-nitrophenyl isocyanate (50% excess) whereby a vigorous $CO_2$ evolution occurred each time. After a reaction time of 24 hours at 20° C. the major portion of the HMPTA was removed by distillation in vacuo. The residue was extracted several times with 2% $NaHCO_3$ solution and then digested with dist. $H_2O$. The resulting residue was dried in vacuo at 40° C. and then extracted several times with warm MeOH until the residue contained merely the difficultly soluble by-product N,N'-bis(p-nitrophenyl) urea. The MeOH extracts were concentrated to 300 ml, whereby some impurities formed a flocculent precipitate. After filtration, the filtrate (330 ml) was purified on a column of "Sephadex LH-20" equilibrated with MeOH. The main fraction of the MeOH eluate was concentrated in vacuo at 30° C. to a small volume, whereby a needle-like substance crystallized. The obtained crystals were filtered off and washed portionwise with 50 ml of ice-cooled MeOH. After drying in a vacuum desiccator at 40° C. over $P_2O_5$ there were obtained 31.1 g (62.1% of the theory) of crystalline compound 2a of m.p. which was homogeneous in SS A and B as shown by TLC. The mother liquor provided a further crop of 5.8 g (11.6% of the theory) of substance 2a of m.p. which was homogeneous in SS A and B as shown by TLC. Elementary analysis and calculation from the empirical formula $C_{25}H_{32}N_4O_7$ gave the following values: C=60.23% (59.99%), H=6.50% (6.44%) and N=11.38% (11.19%).

2b. $CF_3COOH.H$-Lys($\epsilon$-Cbo)-pNA 25.03 g (50 mmoles) of compound 2a were treated, while vigorously stirring, with 50 ml of freshly distilled anhydrous trifluoroacetic acid at 20° C. for 60 min. in the absence of humidity. The BOC group was selectively split off with $CO_2$ evolution and liberation of isobutylene. The reaction solution was added dropwise, while vigorously stirring, to 750 ml of absolute ether, whereby flocculent $CF_3COOH.H$-Lys($\epsilon$-Cbo)-pNA was precipitated. The ethereal phase was sucked off through a filter rod. The solid phase was treated 4 times with portions of 100 ml of absolute ether. The resulting residue was dissolved in 200 ml of MeOH. The pH was adjusted to 4.5 by means of $Et_3N$, and the solution was concentrated to dryness in vacuo at 30° C. The residue was dissolved in 200 ml of MeOH and purified on a column of "Sephadex LH-20" equilibrated with MeOH. The main fraction of the MeOH eluate which was homogeneous in SS C as shown by TLC was concentrated in vacuo at 30° C. The resulting residue was dried in a vacuum desiccator at 40° C. over $P_2O_5$ to obtain 22.64 g (88.0% of the theory) of amorphous compound 2b. Elementary analysis and calculation from the empirical formula $C_{22}H_{25}N_4O_7F_3$ gave the following values: C=51.66% (51.36%), H=4.88% (4.90%) and N=11.08% (10.89%).

2c. BOC-Phe-Lys($\epsilon$-Cbo)-pNA 7.72 g (15 mmoles) of compound 2b were dissolved in 50 ml of freshly distilled DMF and cooled to $-10°$ C. To the solution there were added, while stirring, 6.38 g (16.5 mmoles) of BOC-Phe-OpNP and 2.09 ml (15 mmoles) of $Et_3N$. The mixture was allowed to react for 3 hours in the absence of humidity, whereby the reaction temperature gradually reached room temperature. The solution was again cooled to $-10°$ C. and buffered with 1.05 ml (7.5 mmoles) of $Et_3N$. After a reaction time of 5 hours this procedure was repeated with 1.05 ml of $Et_3N$. After a reaction time of 16 hours at 20° C. the reaction solution was concentrated to dryness in vacuo at 50° C. The residue was dissolved in 150 ml of MeOH and purified by gel filtration on a column of "Sephadex LH-20" equilibrated with MeOH. The first main fraction of the MeOH eluate which was homogeneous in the SS A and B as shown by TLC was concentrated to a small volume in vacuo at 30° C., whereby the desired substance crystallized. The crystals were filtered off and washed portionwise with 30 ml of ice-cooled MeOH. The mother liquor provided an additional amount of 1.0 g of crystalline substance. After drying in a vacuum desiccator at 40° C. over $P_2O_5$ there were obtained 7.72 g (79.5% of the theory) of compound 2c of m.p. which was homogeneous in SS A and B as shown by TLC. Elementary analysis and calculation from the empirical formula $C_{34}H_{41}N_5O_8$ gave the following values: C=62.88% (63.05%), H=6.42% (6.38%) and N=11.06% (10.81%).

2d. $CF_3COOH.Phe$-Lys($\epsilon$-Cbo)-pNA 3.24 g (5 mmoles) of compound 2c were treated, while vigorously stirring, with 10 ml of freshly distilled anhydrous trifluoroacetic acid for 60 minutes at 20° C. in the absence of humidity. The reaction solution was added dropwise, while vigorously stirring, to 100 ml of absolute ether, whereby amorphous $CF_3COOH.H$-Phe-Lys($\epsilon$-Cbo)-pNA was precipitated. The ethereal phase was sucked off. The solid residue was washed 3 times with portions of 30 ml of absolute ether. The resulting residue was dissolved in 50 ml of MeOH. The pH was adjusted to 4.5 by means of $Et_3N$, and the solution was concentrated to dryness in vacuo at 30° C. The residue was dissolved in 75 ml of MeOH and purified on a column of "Sephadex LH-20" equilibrated with MeOH. The main fraction of the MeOH eluate which was homogeneous in SS C as shown by TLC was concentrated in vacuo at 30° C. After drying of the residue in a vacuum desiccator at 40° C. over $P_2O_5$ there were obtained 2.95 g (89.2% of the theory) of amorphous compound 2d. Elementary analysis and calculation from the empirical formula $C_{31}H_{34}N_5O_8F_3$ gave the following values: C=56.82% (56.27%), H=5.16% (5.18%) and N=10.63% (10.59%).

2e. Cbo-D-CHG-Phe-Lys($\epsilon$-Cbo)-pNA 1.99 g (3 mmoles) of compound 2d were dissolved in 15 ml of freshly distilled DMF and cooled to $-10°$ C. To the solution there were added, while stirring, 1.36 g (3.3 mmoles) of Cbo-D-CHG-OpNP and 0.42 ml (3 mmoles) of $Et_3N$. The mixture was allowed to react for 3 hours in the absence of humidity, whereby the temperature gradually reached 20° C. The reaction solution was again cooled to $-10°$ C. and buffered with 0.21 ml (1.5 mmoles) of $Et_3N$. After a reaction time of 5 hours at $-10°$ C., the temperature of the reaction mixture gradually reached room temperature. This procedure was repeated with 0.21 ml of $Et_3N$, whereby the reaction took about 16 hours. The reaction mixture was concentrated to dryness in vacuo at 50° C., and the residue was dissolved in 50 ml of MeOH and purified by gel filtration on a column of "Sephadex LH-20" equilibrated with MeOH. The first main fraction of the MeOH eluate which was homogeneous in SS A and B as shown by TLC was concentrated to dryness in vacuo at 30° C. The residue was dried in a vacuum desiccator at 40° C. over $P_2O_5$ to obtain 2.03 g (82.4% of the theory) of partially crystalline compound 2e. Elementary analysis and calculation from the empirical formula $C_{45}H_{52}N_6O_9$ gave the following values: C=66.22% (65.84%), H=6.32% (6.38%) and N=10.49% (10.24%).

2f. 2HBr.H-D-CHG-Phe-Lys-pNA 1.64 g (2 mmoles) of compound 2e were treated, while stirring, with 12 ml of 2 N HBr glacial acetic acid for 40 minutes at 20° C. in the absence of humidity. The tripeptide derivative gradually dissolved with simultaneous splitting off of the two protective groups Cbo and BOC and $CO_2$ evolution. The reaction solution was added dropwise, while vigorously stirring, to 100 ml of absolute ether, whereby flocculent 2HBr.H-D-CHG-Phe-Lys-pNA was precipitated. The ethereal phase was sucked off after 30 minutes, and the solid phase was washed 4 times with portions of 25 ml of absolute ether. The resulting residue was dissolved in 40 ml of MeOH. The pH was adjusted to 4.5 by means of $Et_3N$, and the solution was concentrated to dryness in vacuo at 30° C. The residue was dissolved in 30 ml of MeOH and purified on a column of "Sephadex LH-20" equilibrated with MeOH. The main fraction of the MeOH eluate which was split by treatment with trypsin with liberation of p-nitroaniline was concentrated to dryness in vacuo at 30° C. For a further purification the pre-purified product was dissolved in 25 ml of 33% AcOH and purified by gel filtration on a column of "Sephadex G-15" equilibrated with 33% AcOH. The fraction of the AcOH eluate which was split by treatment with trypsin with liberation of p-nitroaniline was concentrated to dryness in vacuo at 40° C. The resulting residue was dried in a vacuum desiccator at 40° C. over $P_2O_5$ to obtain 1.13 g (79.1% of the theory) of amorphous substance 2f which was homogeneous in SS C as shown by TLC. Elementary analysis and calculation from the empirical formula $C_{29}H_{42}N_6O_5Br_2$ gave the following values: C=48.41% (48.75%), H=6.02% (5.93%), N=12.11% (11.76%) and Br=22.02% (22.37%).

The amino acid analysis confirmed the presence of the expected amino acids in the correct proportions: Phe: 1.00-Lys: 0.98-D-CHG: 1.02.

EXAMPLE 3

2HBr.H-D-Val-CHA-Arg-MCA 3b. 2HBr.H-Arg-MCA 13.0 g (25.9 mmoles) of commercial Cbo-Arg-MCA.HCl were deblocked according to Example 1b by means of 104 ml (208 mmoles) of a solution of 2 N HBr in glacial acetic acid. The dry residue was dissolved in 400 ml of MeOH and purified on a column of "Sephadex LH-20". The fraction of the MeOH eluate which was split by treatment with trypsin with liberation of 4-methyl-7-amino-coumarin was concentrated to dryness in vacuo at 30° C. The resulting residue was dried in a vacuum desiccator at 40° C. over $P_2O_5$ to obtain 11.2 g (87.7% of the theory) of amorphous compound 3b which was homogeneous in SS C as shown by TLC. Elementary analysis and calculation from the empirical formula $C_{16}H_{23}N_5O_3Br_2$ gave the following values: C=39.40% (38.96%), H=4.61% (4.70%), N=14.48% (14.20%) and Br=31.90% (32.40%).

3c. Cbo-CHA-Arg-MCA.HBr 4.93 g (10 mmoles) of compound 3b and 4.69 g (11 mmoles) of Cbo-CHA-OpNP were added to 75 ml of freshly distilled DMF. After cooling to −10° C., there were added, while stirring, first 1.40 ml (10 mmoles) and then 0.70 ml (5 mmoles) of $Et_3N$. The mixture was allowed to react, in the absence of humidity, first for 3 hours at −10° C. and then for 4 hours at room temperature. The reaction solution was again cooled to −10° C., buffered with 0.70 ml of $Et_3N$ and stirred overnight at 20° C. The reaction mixture was concentrated to dryness in vacuo at 50° C., and the residue was dissolved in 200 ml of 50% AcOH and purified on a column of "Sephadex G-15". The fraction of the AcOH eluate which was split by treatment with trypsin with liberation of 4-methyl-7-amino-coumarin was concentrated to dryness in vacuo at 40° C. The residue thus obtained was dried in a vacuum desiccator at 60° C. over $P_2O_5$ to yield 5.95 g (85.0% of the theory) of crystalline compound 3c of m.p. which was homogeneous in SS C as shown by TLC. Elementary analysis and calculation from the empirical formula $C_{33}H_{43}N_6O_6Br$ gave the following values: C=56.33% (56.65%), H=6.28% (6.19%), N=12.25% (12.01%) and Br=11.30% (11.42%).

3d. 2HBr.H-CHA-Arg-MCA 5.60 g (8 mmoles) of compound 3c were deblocked according to Example 1d by means of 32 ml of 2 N HBr in glacial acetic acid. The resulting crude product was dissolved in 100 ml of MeOH and purified on a column of "Sephadex LH-20". The fraction of the MeOH eluate which was split by treatment with trypsin with liberation of 4-methyl-7-amino-coumarin was concentrated to dryness in vacuo at 30° C. The resulting residue was dried in a vacuum desiccator at 40° C. over $P_2O_5$ to obtain 4.76 g (92.1% of the theory) of amorphous compound 3d which was homogeneous in SS C as shown by TLC. Elementary analysis and calculation from the empirical formula $C_{25}H_{38}N_6O_4Br$ gave the following values: C=47.02% (46.45%), H=6.02% (5.93%), N=13.21% (13.00%) and Br=24.48% (24.72%).

3e. Cbo-D-Val-CHA-Arg-MCA.HBr 3.23 g (5 mmoles) of compound 3d were reacted with 2.05 g (5.5 mmoles) of Cbo-D-Val-OpNP in accordance with Example 1e. The resulting crude product was dissolved in 75 ml of 50% AcOH and purified on a column of "Sephadex G-15". The fraction of the AcOH eluate which was split by treatment with trypsin with liberation of 4-methyl-7-amino-coumarin was concentrated to dryness in vacuo at 40° C. The residue was dried in a vacuum desiccator at 60° C. over $P_2O_5$ to obtain 3.21 g (80.4% of the theory) of amorphous compound 3e which was homogeneous in SS C according to TLC. Elementary analysis and calculation from the empirical formula $C_{38}H_{52}N_7O_7Br$ gave the following values: C=57.05% (57.14%), H=6.61% (6.56%), N=12.49% (12.28%) and Br=9.82% (10.00%).

3f. 2HBr.H-D-Val-CHA-Arg-MCA 2.40 g (3 mmoles) of compound 3d were deblocked according to Example 1f by means of 12 ml of 2 N HBr in glacial acetic acid. The resulting crude product was dissolved in 50 ml of MeOH and purified on a column of "Sephadex LH-20". The fraction of the MeOH eluate which was split by treatment with trypsin with liberation of 4-methyl-7-amino-coumarin was concentrated to dryness in vacuo at 30° C. For a further purification the pre-purified product was dissolved in 40 ml of 50% AcOH and purified by gel filtration on a column of "Sephadex G-15". The main fraction of the AcOH eluate which was split by treatment with trypsin with liberation of 4-methyl-7-amino-coumarin was concentrated to dryness in vacuo at 40° C. The residue was dried in a vacuum desiccator at 40° C. over $P_2O_5$ to obtain 1.73 g (77.3% of the theory) of amorphous compound 3f which was homogeneous in SS C as shown by TLC. Elementary analysis and calculation from the empirical formula $C_{30}H_{47}N_7O_5Br_2$ gave the following values: C=48.12% (48.33%), H=6.43% (6.35%), N=13.38% (13.15%) and Br=21.18% (21.44%).

The amino acid analysis confirmed the presence of the expected amino acids in the correct proportions: Val: 1.00-Arg: 1.02-D-CHA: 0.97.

EXAMPLE 4

2HBr.H-D-CHG-Phe-Lys-MCA

4a. BOC-Lys($\epsilon$-Cbo)-MCA 38.05 g (0.1 mole) of dried BOC-Lys($\epsilon$-Cbo)-OH were dissolved in a 1000 ml three-necked flask in a mixture of 50 ml of freshly distilled anhydrous DMF and 300 ml of absolute THF at 20° C. To the solution, cooled to $-10°$ C., there was added, while stirring, a solution of 10.2 g (0.1 mole) of $Et_3N$ in 75 ml of THF in the absence of humidity. Then a solution of 13.65 g (0.1 mole) of isobutyl chloroformate in 50 ml of THF was added dropwise within 20 minutes, whereby the reaction temperature was never allowed to exceed $-5°$ C. After a reaction time of about 10 minutes at a temperature of $-10°$ C. to $-5°$ C. a solution of 17.52 g (0.1 mole) of 4-methyl-7-amino-coumarin in 75 ml of DMF was added dropwise within 25 minutes, whereby the temperature was never allowed to exceed $-5°$ C. The reaction mixture was then stirred for 1 hour at $-5°$ C. and overnight at room temperature and then again cooled to $-10°$ C. The crystallized $Et_3N.HCl$ was filtered off. The filtrate was concentrated to dryness in vacuo at 50° C. The residue was dissolved in 500 ml of MeOH and purified by gel filtration on a column of "Sephadex LH-20". In addition to the desired product BOC-Lys($\epsilon$-Cb0)-MCA the MeOH eluate provided three further fractions containing the by-product isobutyl N-[4-methyl-coumaryl-(7)]carbaminate and the starting products BOC-Lys($\epsilon$-Cbo)-OH and 7-amino-4-methyl-coumarin, respectively. The fraction containing BOC-Lys($\epsilon$-Cbo)-MCA was concentrated to dryness in vacuo at 30° C. The residue was dried in a vacuum desiccator at 50° C. over $P_2O_5$ to obtain 26.3 g (48.9% of the theory) of partially crystalline compound 4a which was homogeneous in SS A and B as shown by TLC. Elementary analysis and calculation from the empirical formula $C_{29}H_{35}N_3O_7$ gave the following values: C=64.90% (64.79%), H=6.52% (6.56%) and N=7.88% (7.82%).

4b. $CF_3COOH.H$-Lys($\epsilon$-Cbo)-MCA 21.5 g (40 mmoles) of compound 4a were deblocked according to Example 2b by means of 60 ml of trifluoroacetic acid. The resulting crude product was dissolved in 250 ml of MeOH and purified by gel filtration on a column of "Sephadex LH-20". The first main fraction of the MeOH eluate which was homogeneous in SS C as shown by TLC was concentrated to dryness in vacuo at 30° C. The residue was dried in a vacuum desiccator at 40° C. over $P_2O_5$ to obtain 19.5 g (88.4% of the theory) of amorphous compound 4b. Elementary analysis and calculation from the empirical formula $C_{26}H_{28}N_3O_7F_3$ gave the following values: C=57.02% (56.62%), H=5.20% (5.12%) and N=7.58% (7.62%).

4c. BOC-Phe-Lys($\epsilon$-Cbo)-MCA 5.52 g (10 mmoles) of compound 4b were reacted according to Example 2c with 4.25 g (11 mmoles) of BOC-Phe-OpNP. The resulting crude product was dissolved in 100 ml of MeOH and purified by gel filtration on a column of "Sephadex LH-20". The main fraction of the MeOH eluate which was homogeneous in SS A and B as shown by TLC was concentrated to dryness in vacuo at 30° C. The residue was dried in a vaccum desiccator at 50° C. over $P_2O_5$ to obtain 5.78 g (84.4% of the theory) of partially crystalline product 4c. Elementary analysis and calculation from the empirical formula $C_{38}H_{44}N_4O_8$ gave the following values: C=66.09% (66.65%), H=6.44% (6.48%) and N=8.32% (8.18%).

4d. $CF_3COOH.H$-Phe-Lys($\epsilon$-Cbo)-MCA 3.42 g (5 mmoles) of compound 4c were deblocked according to Example 2d by means of 15 ml of trifluoroacetic acid. The resulting crude product was dissolved in 75 ml of MeOH and purified by gel filtration on a column of "Sephadex LH-20". The main fraction of the MeOH eluate which was homogeneous in SS C as shown by TLC was concentrated to dryness in vacuo at 30° C. The residue was dried in a vaccum desiccator at 40° C. over $P_2O_5$ to obtain 3.41 g (97.6% of the theory) of amorphous compound 4d. Elementary analysis and calculation from the empirical formula $C_{35}H_{37}N_4O_8F_3$ gave the following values: C=59.54% (60.16%), H=5.31% (5.34%) and N=8.33% (8.02%).

4e. Cbo-D-CHG-Phe-Lys($\epsilon$-Cbo)-MCA 2.10 g (3 mmoles) of compound 4d were reacted according to Example 2e with 1.36 g (3.3 mmoles) of Cbo-D-CHG-OpNP. The resulting crude product was dissolved in 40 ml of MeOH and purified by gel filtration on a column of "Sephadex LH-20". The first main fraction of the MeOH eluate which was homogeneous in SS A and B as shown by TLC was concentrated to dryness in vacuo at 30° C. The residue was dried in a vacuum desiccator at 60° C. over $P_2O_5$ to obtain 2.12 g (82.4% of the theory) of amorphous compound 4e. Elementary analysis and calculation from the empirical formula $C_{49}H_{55}N_5O_9$ gave the following values: C=69.03% (68.59%), H=6.49% (6.46%) and N=8.32% (8.16%).

4f. 2HBr.H-D-CHG-Phe-Lys-MCA 1.72 g (2 mmoles) of compound 4e were deblocked according to Example 2f by means of 12 ml of 2 N HBr in glacial acetic acid. The resulting crude product was dissolved in 30 ml of MeOH and purified on a column of "Sephadex LH-20". The fraction of the MeOH eluate which was split by treatment with trypsin with liberation of 4-methyl-7-amino-coumarin was concentrated to dryness in vacuo at 30° C. For a further purification the pre-purified product was dissolved in 40 ml of 50% AcOH and purified by gel filtration on a column of "Sephadex G-15". The main fraction of the AcOH eluate which was split by treatment with trypsin with liberation of 4-methyl-7-amino-coumarin was concentrated to dryness in vacuo at 40° C. The residue was dried in a vacuum desiccator at 40° C. over $P_2O_5$ to obtain 1.10 g (73.2% of the theory) of amorphous compound 4f which was homogeneous in SS C as shown by TLC. Elementary analysis and calculation from the empirical formula $C_{33}H_{45}N_5O_5Br_2$ gave the following values: C=53.20% (52.74%), H=6.12% (6.04%), N=9.18% (9.32%) and Br=21.16% (21.26%).

The amino acid analysis confirmed the presence of the expected amino acids in the correct proportions: Phe: 1.00-Lys: 0.99-D-CHG: 0.97.

EXAMPLE 5

2HBr.H-D-Val-CHA-Arg-DPA

5a. Cbo-Arg-DPA.HCl 34.48 g (0.1 mole) of dried Cbo-Arg-OH.HCl were dissolved in a 1000 ml three-necked flask in a mixture of 150 ml of freshly distilled anhydrous DMF and 300 ml of absolute THF at 20° C. To the solution cooled to −10° C. there were added, while stirring, 10.2 g (0.1 mole) of Et$_3$N in the absence of humidity. Then a solution of 13.65 g (0.1 mole) of isobutyl chloroformate in 50 ml of THF was added dropwise within 20 minutes, whereby the reaction temperature was never allowed to exceed −5° C. After an additional reaction time of 10 minutes at a temperature of −10° C. to −5° C. a solution of 20.92 g (0.1 mole) of dimethyl 5-amino-isophthalate in 75 ml of DMF was added dropwise within 30 minutes, whereby the reaction temperature was always kept below −5° C. The reaction mixture was allowed to react for one further hour at −5° C. It was stirred overnight at 20° C. and then cooled to −15° C. in order to allow Et$_3$N.HCl to crystallize. The formed Et$_3$N.HCl was filtered off and washed with a small quantity of cold DMF. The filtrate and the washing solution were together concentrated to dryness in vacuo at 50° C. The residue was dissolved in 1000 ml of 50% AcOH and purified by gel filtration on a column of "Sephadex G-15" equilibrated with 50% AcOH. The main fraction of the AcOH eluate which was split by treatment with trypsin with liberation of dimethyl 5-amino-isophthalate was concentrated to dryness in vacuo at 40° C. The residue was dried in a vacuum desiccator at 50° C. over $P_2O_5$ to give 24.6 g (45.9% of the theory) of amorphous compound 5a which was homogeneous in SS C as shown by TLC. Elementary analysis and calculation from the empirical formula $C_{24}H_{30}N_5O_7Cl$ gave the following values: C=53.21% (53.78%), H=5.71% (5.64%), N=13.20% (13.07%) and Cl=6.52% (6.62%).

5b. 2HBr.H-Arg-DPA 21.44 g (40 mmoles) of compound 5a were deblocked according to Example 1b. After the usual treatment the resulting crude product was dissolved in 250 ml of MeOH and purified by gel filtration on a column of "Sephadex LH-20". The fraction of the MeOH eluate which was split by treatment with trypsin with liberation of dimethyl 5-amino-isophthalate was concentrated to dryness in vacuo. The residue was dried in a vacuum desiccator at 40° C. over $P_2O_5$ to give 19.63% (93.1% of the theory) of amorphous compound 5b which was homogeneous in SS C as shown by TLC. Elementary analysis and calculation from the empirical formula $C_{16}H_{25}N_5O_5Br_2$ gave the following values: C=36.82% (36.45%), H=4.67% (4.78%), N=13.45% (13.28%) and Br=29.85% (30.31%).

5c. Cbo-CHA-Arg-DPA.HBr 5.27 g (10 mmoles) of compound 5b were reacted according to Example 1c with 4.69 g (11 mmoles) of Cbo-CHA-OpNP. The crude product obtained after the usual treatment was dissolved in 200 ml of 50% AcOH and purified on a column of "Sephadex G-15". The fraction of the AcOH eluate which was split by treatment with trypsin with liberation of dimethyl 5-aminoisophthalate was concentrated to dryness in vacuo at 40° C. The residue was dried in a vacuum desiccator at 60° C. over $P_2O_5$ to give 6.06 g (82.6% of the theory) of amorphous compound 5c which was homogeneous in SS C as shown by TLC. Elementary analysis and calculation from the empirical formula $C_{33}H_{45}N_6O_8Br$ gave the following values: C=53.74% (54.02%), H=6.28% (6.18%), N=11.90% (11.46%) and Br=10.68% (10.89%).

5d. 2HBr.H-CHA-Arg-DPA 5.87 g (8 mmoles) of compound 5c were deblocked according to Example 1d by means of 32 ml of 2 N HBr in glacial acetic acid. The crude product obtained after the usual treatment was dissolved in 100 ml of MeOH and purified on a column of "Sephadex LH-20". The fraction of the MeOH eluate which was split by treatment with trypsin with liberation of dimethyl 5-amino-isophthalate was concentrated to dryness in vacuo at 30° C. The residue was dried in a vacuum desiccator at 40° C. over $P_2O_5$ to give 4.79 g (88.0% of the theory) of amorphous compound 5d which was homogeneous in SS C as shown by TLC. Elementary analysis and calculation from the empirical formula $C_{25}H_{40}N_6O_6Br$ gave the following values: C=43.75% (44.13%), H=5.88% (5.93%), N=12.69% (12.35%) and Br=23.22% (23.49%).

5e. Cbo-D-Val-CHA-Arg-DPA.HBr 3.40 g (5 mmoles) of compound 5d were reacted according to Example 1e with 2.05 g (5.5 mmoles) of Cbo-D-Val-OpNP. The crude product obtained after the usual treatment was dissolved in 100 ml of 50% AcOH and purified on a column of "Sephadex G-15". The fraction of the AcOH eluate which was split by treatment with trypsin with liberation of dimethyl 5-aminoisophthalate was concentrated to dryness in vacuo at 40° C. The residue was dried in a vacuum desiccator at 60° C. over $P_2O_5$ to give 3.25 g (78.1% of the theory) of amorphous compound 5e which was homogeneous in SS C as shown by TLC. Elementary analysis and calculation from the empirical formula $C_{38}H_{54}N_7O_9Br$ gave the following values: C=53.95% (54.80%), H=6.65% (6.54%), N=12.07% (11.77%) and Br=9.38% (9.59%).

5f. 2HBr.H-D-Val-CHA-Arg-DPA 2.50 g (3 mmoles) of compound 5e were deblocked according to Example 1f by means of 12 ml of 2 N HBr in glacial acetic acid. The crude product obtained after the usual treatment was dissolved in 50 ml of MeOH and pre-purified on a column of "Sephadex LH-20". The fraction of the MeOH eluate which was split by treatment with trypsin with liberation of dimethyl 5-amino-isophthalate was concentrated to dryness in vacuo at 30° C. The pre-purified product was dissolved in 50 ml of 50% AcOH and purified by gel filtration on a column of "Sephadex G-15". The main fraction of the AcOH eluate which was split by treatment with trypsin with liberation of dimethyl 5-amino-isophthalate was concentrated to dryness in vacuo at 40° C. The residue was dried in a vacuum desiccator at 40° C. over $P_2O_5$ to give 1.93 g (82.6% of the theory) of amorphous compound 5f which was homogeneous in SS C as shown by TLC. Elementary analysis and calculation from the empirical formula $C_{30}H_{49}N_7O_7Br_2$ gave the following values: C=46.84% (46.22%), H=6.42% (6.34%), N=12.16% (12.58%) and Br=20.22% (20.50%).

The amino acid analysis confirmed the presence of the expected amino acids in the correct proportions: D-Val: 1.00-Arg: 0.98-CHA: 1.02.

EXAMPLE 6

2HBr.H-D-CHG-Phe-Lys-DPA

6a. BOC-Lys($\epsilon$-Cbo)-DPA 38.05 g (0.1 mole) of dried BOC-Lys($\epsilon$-Cbo)-OH were dissolved in a 1000 ml three-necked flask in a mixture of freshly distilled anhydrous DMF and 300 ml of absolute THF at 20° C. To the solution cooled to −10° C. there was added, while stirring, a solution of 10.2 g (0.1 mole) of Et$_3$N in 75 ml of THF in the absence of humidity. Then a solution of 13.65 g (0.1 mole) of isobutyl chloroformate in 50 ml of THF was added dropwise within 20 minutes, whereby the reaction temperature was not allowed to exceed −5° C. After a reaction time of about 10 minutes at −10° C. to −5° C. a solution of 20.92 g (0.1 mole) of dimethyl 5-amino-isophthalate in 75 ml of DMF was added dropwise within 30 minutes. The reaction mixture was further treated according to Example 4a. The resulting residue was dissolved in 500 ml of MeOH and purified by gel filtration on a column of "Sephadex LH-20". In addition to the desired product BOC-Lys($\epsilon$-Cbo)-DPA the MeOH eluate contained three further products, viz. the by-product isobutyl N-[1,3-dimethoxycarbonylphenyl-(5)]-carbaminate and the two starting products BOC-Lys-($\epsilon$-Cbo)-OH and dimethyl 5-amino-isophthalate, respectively, in three different fractions. The fraction containing BOC-Lys-($\epsilon$-Cbo)-DPA was concentrated to dryness in vacuo at 30° C. The residue was dried in a vacuum desiccator at 50° C. over P$_2$O$_5$ to obtain 27.4 g (47.9% of the theory) of crystalline compound 6a of m.p. which was homogeneous in SS A and B as shown by TLC. Elementary analysis and calculation from the empirical formula $C_{29}H_{37}N_3O_9$ gave the following values: C=60.58% (60.93%), H=6.53% (6.52%) and N=7.48% (7.35%).

6b. CF$_3$COOH.H-Lys($\epsilon$-Cbo)-DPA 22.87 g (40 mmoles) of compound 4a were deblocked according to Example 2b by means of 70 ml of trifluoroacetic acid. The crude product obtained after the usual treatment was dissolved in 250 ml of MeOH and purified by gel filtration on a column of "Sephadex LH-20". The main fraction of the MeOH eluate which was homogeneous in SS C as shown in TLC was concentrated to dryness in vacuo at 30° C. The residue was dried in a vacuum desiccator at 40° C. over P$_2$O$_5$ to obtain 20.7 g (88.4% of the theory) of amorphous compound 6b. Elementary analysis and calculation from the empirical formula $C_{26}H_{30}N_3O_9F_3$ gave the following values: C=52.77% (53.33%), H=5.25% (5.16%) and N=7.02% (7.18%).

6c. BOC-Phe-Lys($\epsilon$-Cbo)-DPA 5.86 g (10 mmoles) of compound 6b were reacted according to Example 2c with 4.25 g (11 mmoles) of BOC-Phe-OpNP. The crude product obtained after the usual treatment was dissolved in 100 ml of MeOH and purified by gel filtration on a column of "Sephadex LH-20". The first main fraction of the MeOH eluate which was homogeneous in SS A and B as shown by TLC was concentrated to dryness in vacuo at 30° C. The residue was dried in a vacuum desiccator at 50° C. to obtain 5.87 g (81.7% of the theory) of crystalline compound 6c. Elementary analysis and calculation from the empirical formula $C_{38}H_{46}N_4O_{10}$ gave the following values: C=63.82% (63.50%), H=6.49% (6.45%) and N=7.64% (7.80%).

6d. CF$_3$COOH.Phe-Lys($\epsilon$-Cbo)-DPA 3.59 g (5 mmoles) of compound 6c were deblocked according to Example 2d by means of 15 ml of trifluoroacetic acid. The crude product obtained after the usual treatment was dissolved in 60 ml of MeOH and purified by gel filtration on a column of "Sephadex LH-20". The main fraction of the MeOH eluate which was homogeneous in SS C as shown by TLC was concentrated to dryness in vacuo at 30° C. The residue was dried in a vacuum desiccator at 40° C. over P$_2$O$_5$ to obtain 3.40 g (92.8% of the theory) of amorphous compound 6d. Elementary analysis and calculation from the empirical formula $C_{35}H_{39}N_4O_{10}F_3$ gave the following values: C=57.11% (57.37%), H=5.40% (5.36%) and N=7.79% (7.65%).

6e. Cbo-D-CHG-Phe-Lys($\epsilon$-Cbo)-DPA 2.20 g (3 mmoles) of compound 6d were reacted according to Example 2e with 1.36 g (3.3 mmoles) of Cbo-D-CHG-OpNP. The crude product obtained after the usual treatment was dissolved in 60 ml of MeOH and purified by gel filtration on a column of "Sephadex LH-20". The first main fraction of the MeOH eluate which was homogeneous in SS A and B as shown by TLC was concentrated to dryness in vacuo at 30° C. The residue was dried in a vacuum desiccator at 60° C. over P$_2$O$_5$ to obtain 2.07 g (77.4% of the theory) of partially crystalline compound 6e. Elementary analysis and calculation from the empirical formula $C_{49}H_{57}N_5O_{11}$ gave the following values: C=66.18% (65.98%), H=6.52% (6.44%) and N=7.59% (7.85%).

6f. 2HBr.H-D-CHG-Phe-Lys-DPA 892 mg (1 mmole) of compound 6e were deblocked according to Example 2f by means of 6 ml of 2 N HBr in glacial acetic acid. The crude product obtained after the usual treatment was dissolved in 20 ml of MeOH and pre-purified on a column of "Sephadex LH-20". The fraction of the MeOH eluate which was split by treatment with trypsin with liberation of dimethyl 5-amino-isophthalate was concentrated to dryness at 30° C. For a further purification the pre-purified product was dissolved in 30 ml of 50% AcOH and purified by gel filtration on a column of "Sephadex G-15". The main fraction of the AcOH eluate which was split by treatment with trypsin with liberation of dimethyl 5-amino-isophthalate was concentrated to dryness in vacuo at 40° C. The residue was dried in a vacuum desiccator at 40° C. over P$_2$O$_5$ to obtain 602 mg (76.6% of the theory) of amorphous compound 6f which was homogeneous in SS C as shown by TLC. Elementary analysis and calculation from the empirical formula $C_{33}H_{47}N_5O_7Br_2$ gave the following values: C=49.79% (50.45%), H=6.10% (6.03%), N=9.09% (8.92%) and Br=19.87% (20.34%).

The amino acid analysis confirmed the presence of the expected amino acids in the correct proportions: Phe: 1.00-Lys: 1.01-D-CHG: 0.97.

EXAMPLE 7

2HBr.H-D-Val-CHA-Arg-2-NA

7b. 2HBr.H-Arg-2-NA 9.40 g (20 mmoles) of commercial Cbo-Arg-2-NA.HCl were deblocked according to Example 1b with a solution of 80 ml of 2 N HBr in glacial acetic acid. The product obtained after the usual treatment was dissolved in 150 ml of MeOH and purified on a column of "Sephadex LH-20". The fraction of the MeOH eluate which was split by treatment with trypsin with liberation of 2-naphthylamine was concentrated to dryness in vacuo at 30° C. The residue was dried in a vacuum desiccator at 40° C. over $P_2O_5$ to obtain 8.60 g (93.2% of the theory) of amorphous compound 7b which was homogeneous in SS C as shown by TLC. Elementary analysis and calculation from the empirical formula $C_{16}H_{23}N_5OBr_2$ gave the following values: C=42.08% (41.67%), H=5.12% (5.03%), N=14.68% (15.19%) and Br=33.96% (34.65%).

7c. Cbo-CHA-Arg-2-Na.HBr 4.6 g (10 mmoles) of compound 7b were reacted according to Example 1c with 4.69 g (11 mmoles) of Cbo-CHA-OpNP. The crude product obtained after the usual treatment was dissolved in 150 ml of 50% AcOH and purified on a column of "Sephadex G-15". The fraction of the AcOH eluate which was split by treatment with trypsin with liberation of 2-naphthylamine was concentrated to dryness in vacuo at 40° C. The residue was dried in a vacuum desiccator at 60° C. over $P_2O_5$ to obtain 5.31 g (79.5% of the theory) of amorphous compound 7c which was homogeneous in SS C as shown by TLC. Elementary analysis and calculation from the empirical formula $C_{33}H_{43}N_6O_4Br$ gave the following values: C=59.18% (59.37%), H=6.58% (6.49%), N=12.87% (12.59%) and Br=11.55% (11.97%).

7d. 2HBr.H-CHA-Arg-2-NA 4.67 g (7 mmoles) of compound 7c were deblocked according to Example 1d by means of 28 ml of 2 N HBr in glacial acetic acid. The crude product obtained after the usual treatment was dissolved in 100 ml of MeOH and purified on a column of "Sephadex LH-20". The fraction of the MeOH eluate which was split by treatment with trypsin with liberation of 2-napthylamine was concentrated to dryness in vacuo at 30° C. The residue was dried in a vacuum desiccator at 40° C. over $P_2O_5$ to give 3.95 g (91.8% of the theory) of amorphous compound 7d which was homogeneous in SS C as shown by TLC. Elementary analysis and calculation from the empirical formula $C_{25}H_{38}N_6O_2Br_2$ gave the following values: C=49.22% (48.87%), H=6.30% (6.23%), N=13.61% (13.68%) and Br=25.84% (26.01%).

7e. Cbo-D-Val-CHA-Arg-2-NA.HBr 3.07 g (5 mmoles) of compound 7d were reacted according to Example 1e with 2.05 g (5.5 mmoles) of Cbo-D-Val-OpNP. The crude product obtained after the usual treatment was dissolved in 100 ml of 50% AcOH and purified on a column of "Sephadex G-15". The first main fraction of the AcOH eluate which was split by treatment with trypsin with liberation of 2-naphthylamine was concentrated to dryness in vacuo at 40° C. and dried in a vacuum desiccator at 60° C. over $P_2O_5$. There were thus obtained 3.14 g (81.9% of the theory) of amorphous compound 7e which was homogeneous in SS C as shown by TLC. Elementary analysis and calculation from the empirical formula $C_{38}H_{52}N_7O_5Br$ gave the following values: C=58.92% (59.52%), H=6.93% (6.84%), N=13.02% (12.79%) and Br=10.18% (10.42%).

7f. 2HBr.H-D-Val-CHA.Arg-2-NA 1.53 g (2 mmoles) of compound 7e were deblocked according to Example 1f by means of 8 ml of 2 N HBr in glacial acetic acid. The crude product obtained after the usual treatment was dissolved in 40 ml of MeOH and purified on a column of "Sephadex LH-20". The main fraction of the MeOH eluate which was split by treatment with trypsin with formation of 2-naphthylamine was concentrated to dryness in vacuo at 30° C. This product was dissolved in 50 ml of 50% AcOH and purified on a column of "Sephadex G-15". The main fraction of the AcOH eluate which was split by treatment with trypsin with formation of 2-naphthylamine was concentrated to dryness in vacuo at 40° C. The residue was dried in a vacuum desiccator at 40° C. over $P_2O_5$ to give 1.05 g (73.6% of the theory) of amorphous compound 7f which was homogeneous in SS C as shown by TLC. Elementary analysis and calculation from the empirical formula $C_{30}H_{47}N_7O_3Br_2$ gave the following values: C=50.16% (50.50%), H=6.71% (6.64%), N=14.00% (13.74%) and Br=22.05% (22.40%).

The amino acid analysis confirmed the presence of the expected amino acids in the correct proportions: D-Val: 1.00-Arg: 0.98-CHA: 0.97.

EXAMPLE 8

2HBr.H-D-CHG-Phe-Lys-2-NA

8a. BOC.Lys(ε-Cbo)-2-NA 38.05 g (0.1 mole) of BOC-Lys(ε-Cbo)-OH were reacted according to Example 4a with 14.32 g (0.1 mole) of 2-naphthylamine. The residue obtained after the usual treatment was dissolved in 500 ml of MeOH and purified on a column of "Sephadex LH-20". In addition to the desired product BOC-Lys(ε-Cbo)-2-NA the MeOH eluate yielded three further products, viz. the by-product isobutyl N-[1,3-dimethoxy-phenyl-(5)]-carbaminate and the two starting products BOC-Lys(ε-Cbo)-OH and 2-naphthylamine, respectively, in three different fractions. The fraction containing BOC-Lys(ε-Cbo)-2-NA was concentrated in vacuo at 30° C. After drying of the residue in a vacuum desiccator at 50° C. over $P_2O_5$ there were obtained 26.9 g (53.2% of theory) of crystalline compound 8a of m.p. which was homogeneous in the SS A and B as shown by TLC. Elementary analysis and calculation from the empirical formula $C_{29}H_{35}N_3O_5$ gave the following values: C=68.23% (68.89%), H=7.07% (6.98%) and N=8.52% (8.31%).

8b. $CF_3COOH$.H-Lys(ε-Cbo)-2-NA 20.22 g (40 mmoles) of compound 8a were deblocked according to Example 2b by means of 75 ml of trifluoroacetic acid. The crude product obtained after the usual treatment was dissolved in 250 ml of MeOH and purified on a column of "Sephadex LH-20". The main fraction of the MeOH eluate which was homogeneous in SS C as shown by TLC was concentrated to dryness in vacuo at 30° C. After drying of the residue in a vacuum desiccator at 40° C. over $P_2O_5$ there were obtained 18.29 g (88.0% of the theory) of amorphous compound 8b. Elementary analysis and calculation from the empirical formula $C_{26}H_{28}N_3O_5F_3$ gave the following values: C=59.70% (60.11%), H=5.38% (5.43%) and N=8.26% (8.09%).

8c. BOC-Phe-Lys($\epsilon$-Cbo)-2-NA 5.20 g (10 mmoles) of compound 8b were reacted according to Example 2c with 4.25 g (11 mmoles) of BOC-Phe-OpNP. The crude product obtained after the usual treatment was dissolved in 100 ml of MeOH and purified on a column of "Sephadex LH-20". The first main fraction of the MeOH eluate which was homogeneous in SS A and B as shown by TLC was concentrated to dryness in vacuo at 30° C. The residue was dried in a vacuum desiccator at 50° C. over $P_2O_5$. There were thus obtained 5.48 g (83.9% of the theory) of partially crystalline compound 8c. Elementary analysis and calculation from the empirical formula $C_{38}H_{44}N_4O_6$ gave the following values: C=70.41% (69.92%), H=6.74% (6.79%) and N=8.69% (8.58%).

8d. $CF_3COOH.H$-Phe-Lys($\epsilon$-Cbo)-2-NA 3.26 g (5 mmoles) of compound 8c were deblocked according to Example 2d by means of 17 ml of trifluoroacetic acid. The crude product obtained after the usual treatment was dissolved in 75 ml of MeOH and purified on a column of "Sephadex LH-20". The main fraction of the MeOH-eluate which was homogeneous in SS C as shown by TLC was concentrated to dryness in vacuo at 30° C. The residue was dried in a vacuum desiccator at 40° C. over $P_2O_5$ to obtain 3.18 g (95.4% of the theory) of amorphous compound 8d. Elementary analysis and calculation from the empirical formula $C_{35}H_{37}N_4O_6F_3$ gave the following values: C=62.63% (63.05%), H=5.66% (5.59%) and N=8.19% (8.40%).

8e. Cbo-D-CHG-Phe-Lys($\epsilon$-Cbo)-2-NA 1.67 g (2.5 mmoles) of compound 8d were reacted according to Example 2e with 1.14 g (2.76 mmoles) of Cbo-D-CHG-OpNP. The crude product obtained after the usual treatment was dissolved in 50 ml of MeOH and purified on a column of "Sephadex LH-20". The first main fraction of the MeOH eluate which was homogeneous in SS A and B as shown by TLC was concentrated to dryness in vacuo at 30° C. The residue was dried in a vacuum desiccator at 60° C. over $P_2O_5$. There were thus obtained 1.58 g (76.5% of the theory) of amorphous compound 8e. Elementary analysis and calculation from the empirical formula $C_{49}H_{55}N_5O_7$ gave the following values: C=70.91% (71.25%), H=6.66% (6.71%) and N=8.69% (8.48%).

8f. 2HBr.H-D-CHG-Phe-Lys-2-NA 1.24 g (1.5 mmoles) of compound 8e were deblocked according to Example 2f by means of 9 ml of 2 N HBr in glacial acetic acid. The crude product obtained after the usual treatment was dissolved in 25 ml of MeOH and pre-purified on a column of "Sephadex LH-20". The main fraction of the MeOH eluate which was split by treatment with trypsin with liberation of 2-naphthylamine was concentrated to dryness at 30° C. The prepurified product was dissolved in 40 ml of 50% AcOH and further purified on a column of "Sephadex G-15". The main fraction of the AcOH eluate which formed 2-naphthylamine under the action of trypsin was concentrated to dryness in vacuo at 40° C. The residue was dried in a vacuum desiccator at 40° C. over $P_2O_5$ to give 805 mg (74.6% of the theory) of amorphous compound 8f which was homogeneous in SS C as shown by TLC. Elementary analysis and calculation from the empirical formula $C_{33}H_{45}N_5O_3Br_2$ gave the following values: C=54.73% (55.08%), H=6.38% (6.30%), N=10.05% (9.73%) and Br=21.88% (22.21%).

The amino acid analysis confirmed the presence of the expected amino acids in the correct proportions: Phe: 1.00-Lys: 0.99-D-CHG: 0.98.

EXAMPLE 9

2HBr.H-D-Val-CHA-Arg-4-MeO-2-NA 9b. 2HBr.H-Arg-4-MeO-2-NA 10.0 g (20 mmoles) of commercial Cbo-Arg-4-MeO-2-NA. HCl were deblocked according to Example 1b by means of 80 ml of 2 N HBr in glacial acetic acid. The crude product obtained after the usual treatment was dissolved in 150 ml of MeOH and purified on a column of "Sephadex LH-20". The main fraction of the MeOH eluate which was split by treatment with trypsin with liberation of 4-methoxy-2-naphthylamine was concentrated to dryness in vacuo at 30° C. After drying of the residue in a vacuum desiccator at 40° C. over $P_2O_5$ there were obtained 8.98 g (91.4% of the theory) of amorphous compound 9b which was homogeneous in SS C as shown by TLC. Elementary analysis and calculation from the empirical formula $C_{17}H_{25}N_5O_2Br_2$ gave the following values: C=41.22% (41.57%), H=5.19% (5.13%), N=14.40% (14.26%) and Br=32.01% (32.53%).

9c. Cbo-CHA-Arg-4-MeO-2-NA.HBr 4.91 g (10 mmoles) of compound 9b were reacted according to Example 1c with 4.69 g (11 mmoles) of Cbo-CHA-OpNP. The crude product obtained after the usual treatment was dissolved in 150 ml of 50% AcOH and purified on a column of "Sephadex G-15". The first main fraction of the AcOH eluate which was split by treatment with trypsin with liberation of 4-methoxy-2-naphthylamine was concentrated to dryness in vacuo at 40° C. After drying of the residue in a vacuum desiccator at 60° C. over $P_2O_5$ there were obtained 5.36 g (76.8% of the theory) of amorphous compound 9c which was homogeneous in SS C as shown by TLC. Elementary analysis and calculation from the empirical formula $C_{34}H_{45}N_6O_5Br$ gave the following values: C=58.85% (58.53%), H=6.59% (6.50%), N=11.91% (12.05%) and Br=11.32% (11.45%).

9d. 2HBr.H-CHA-Arg-4-MeO-2-NA 4.88 g (7 mmoles) of compound 9c were deblocked according to Example 1d by means of 28 ml of 2 N HBr in glacial acetic acid. The crude product obtained after the usual treatment was dissolved in 100 ml of MeOH and purified on a column of "Sephadex LH-20". The main fraction of the MeOH eluate which was split by treatment with trypsin with formation of 4-methoxy-2-naphthylamine was concentrated to dryness in vacuo at 30° C. After drying of the residue in a vacuum desiccator at 40° C. over $P_2O_5$ there were obtained 4.12 g (91.3% of the theory) of amorphous compound 9d which was homogeneous in SS C as shown by TLC. Elementary analysis and calculation from the empirical formula $C_{26}H_{40}N_6O_3Br_2$ gave the following values: C=48.92% (48.46%), H=6.36% (6.26%), N=12.84% (13.04%) and Br=24.33% (24.80%).

9e. Cbo-D-Val-CHA-Arg-4-MeO-2-NA.HBr 3.22 g (5 mmoles) of compound 9d were reacted according to Example 1e with 2.05 g (5.5 mmoles) of Cbo-D-Val-OpNP. The crude product obtained after the usual treatment was dissolved in 125 ml of 50% AcOH and purified on a column of "Sephadex G-15". The first main fraction of the AcOH eluate which was split by treatment with trypsin with liberation of 4-methoxy-2-naphthylamine was concentrated to dryness in vacuo at 40° C. After drying of the residue in a vacuum desiccator at 60° C. over $P_2O_5$ there were obtained 3.15 g (79.1% of the theory) of amorphous compound 9e which was homogeneous in SS C as shown by TLC. Elementary analysis and calculation from the empirical formula $C_{39}H_{54}N_7O_6Br$ gave the following values: C=58.35% (58.79%), H=6.78% (6.83%), N=12.68% (12.31%) and Br=9.82% (10.03%).

9f. 2HBr.H-D-Val-CHA-Arg-4-MeO-2-NA 1.59 g (2 mmoles) of compound 9e were deblocked according to Example 1f by means of 8 ml of 2 N HBr in glacial acetic acid. The crude product obtained after the usual treatment was dissolved in 40 ml of MeOH and pre-purified on a column of "Sephadex LH-20". The main fraction of the MeOH eluate which was split by treatment with trypsin with formation of 4-methoxy-2-naphthylamine was concentrated to dryness at 30° C. This pre-purified product was dissolved in 60 ml of 50% AcOH and purified on a column of "Sephadex G-15". The main fraction of the AcOH eluate which was split by treatment with trypsin with formation of 4-methoxy-2-naphthylamine was concentrated to dryness in vacuo at 40° C. After drying of the residue in a vacuum desiccator at 40° C. over $P_2O_5$ there were obtained 1.09 g (73.3% of the theory) of amorphous compound 9f which was homogeneous in SS C as shown by TLC. Elementary analysis and calculation from the empirical formula $C_{31}H_{49}N_7O_4Br_2$ gave the following values: C=49.63% (50.07%), H=6.70% (6.64%), N=13.42% (13.19%) and Br=21.22% (21.49%).

The amino acid analysis confirmed the presence of the expected amino acids in the correct proportions: D-Val: 1.00-Arg: 1.01-D-CHA: 0.98.

EXAMPLE 10

2HBr.H-D-CHG-Phe-Lys-4-MeO-2-NA

10a. BOC-Lys(ε-Cbo)-4-MeO-2-NA 9.51 g (25 mmoles) of BOC-Lys(ε-Cbo)-OH were reacted according to Example 4a with 4.33 g (25 mmoles) of 4-methoxy-2-naphthylamine. After the usual treatment the residue was dissolved in 175 ml of MeOH and purified on a column of "Sephadex LH-20". In addition to the desired product BOC-Lys(ε-Cbo)-4-MeO-2-NA the MeOH eluate yielded three further products, viz. the by-product isobutyl N-(4-methoxy-2-naphthyl)-carbaminate as well as the two starting products BOC-Lys(ε-Cbo)-OH and 4-methoxy-2-naphthylamine, respectively, in three different fractions. The fraction containing the desired product was concentrated in vacuo at 30° C. After drying of the residue in a vacuum desiccator at 50° C. over $P_2O_5$ there were obtained 6.28 g (46.9% of the theory) of partially crystalline compound 10a which was homogeneous in SS A and B as shown by TLC. Elementary analysis and calculation from the empirical formula $C_{30}H_{37}N_3O_6$ gave the following values: C=66.83% (67.27%), H=7.04% (6.96%) and N=8.09% (7.85%).

10b. $CF_3COOH.H$-Lys(ε-Cbo)-4-MeO-2-NA 5.36 g (10 mmoles) of compound 10a were deblocked according to Example 2b by means of 20 ml of trifluoroacetic acid. The crude product obtained after the usual treatment was dissolved in 75 ml of MeOH and purified on a column of "Sephadex LH-20". The main fraction of the MeOH eluate which was homogeneous in SS C as shown by TLC was concentrated to dryness in vacuo at 30° C. After drying of the residue in a vacuum desiccator at 40° C. over $P_2O_5$ there were obtained 5.10 g (92.8% of the theory) of amorphous compound 10b. Elementary analysis and calculation from the empirical formula $C_{27}H_{30}N_3O_6F$ gave the following values: C=58.66% (59.01%), H=5.61% (5.50%) and N=7.92% (7.65%).

10c. BOC-Phe-Lys(ε-Cbo)-4-MeO-2-NA 4.40 g (8 mmoles) of compound 10b were reacted according to Example 2c with 3.40 g (8.8 mmoles) of BOC-Phe-OpNP. The crude product obtained after the usual treatment was dissolved in 75 ml of MeOH and purified on a column of "Sephadex LH-20". The first main fraction of the MeOH eluate which was homogeneous in SS A and B as shown by TLC was concentrated to dryness in vacuo at 30° C. After drying of the residue in a vacuum desiccator at 50° C. over $P_2O_5$ there were obtained 4.54 g (83.1% of the theory) of amorphous compound 10c. Elementary analysis and calculation from the empirical formula $C_{39}H_{46}N_4O_7$ gave the following values: C=68.24% (68.60%), H=6.85% (6.79%) and N=8.41% (8.21%).

10d. $CF_3COOH.H$-Phe-Lys(ε-Cbo)-4-MeO-2-NA 3.41 g (5 mmoles) of compound 10c were deblocked according to Example 2d by means of 20 ml of trifluoroacetic acid. The crude product obtained after the usual treatment was dissolved in 80 ml of MeOH and purified on a column of "Sephadex LH-20". The main fraction of the MeOH eluate which was homogeneous in SS C as shown by TLC was concentrated to dryness in vacuo at 30° C. After drying of the residue in a vacuum desiccator at 40° C. over $P_2O_5$ there were obtained 3.29 g (94.4% of the theory) of amorphous compound 10d. Elementary analysis and calculation from the empirical formula $C_{36}H_{39}N_4O_7F_3$ gave the following values: C=61.82% (62.06%), H=5.63% (5.64%) and N=8.21% (8.04%).

10e. Cbo-D-CHG-Phe-Lys(ε-Cbo)-4-MeO-2-NA 1.74 g (2.5 mmoles) of compound 10d were reacted according to Example 2e with 1.14 g (2.76 mmoles) of Cbo-D-CHG-OpNP. The crude product obtained after the usual treatment was dissolved in 60 ml of MeOH and purified on a column of "Sephadex LH-20". The first main fraction of the MeOH eluate which was homogeneous in SS A and B as shown by TLC was concentrated to dryness in vacuo at 30° C. After drying of the residue in a vacuum desiccator at 60° C. over $P_2O_5$ there were obtained 1.76 g (82.2% of the theory) of amorphous compound 10e. Elementary analysis and calculation from the empirical formula $C_{50}H_{57}N_5O_8$ gave the following values: C=69.75% (70.15%), H=6.82% (6.71%) and N=8.28% (8.18%).

10f. 2HBr.H-D-CHG-Phe-Lys-4-MeO-2-NA 856 mg (1 mmole) of compound 10e were deblocked according to Example 2f by means of 6 ml of 2 N HBr in glacial acetic acid. The crude product obtained after the usual treatment was dissolved in 20 ml of AcOH and pre-purified on a column of "Sephadex LH-20". The main fraction of the AcOH eluate which was split by treatment with trypsin with liberation of 4-methoxy-2-naphthylamine was concentrated to dryness at 30° C. The pre-purified product was dissolved in 30 ml of 50% AcOH and purified on a column of "Sephadex G-15". The main fraction of the AcOH eluate which, under the action of trypsin, formed 4-methoxy-2-naphthylamine was concentrated to dryness in vacuo at 40° C. The residue was dried in a vacuum desiccator at 40° C. over $P_2O_5$ to obtain 553 mg (73.8% of the theory) of amorphous compound 10f which was homogeneous in SS C as shown by TLC. Elementary analysis and calculation from the empirical formula $C_{34}H_{47}N_5O_4Br_2$ gave the following values: C=54.09% (54.48%), H=6.31% (6.32%), N=9.52% (9.34%) and Br=20.86% (21.32%).

The amino acid analysis confirmed the presence of the expected amino acids in the correct proportions: Phe: 1.00-Lys: 1.02-D-CHG: 0.99.

A series of other tripeptide derivatives was prepared according to the methods disclosed in the preceding Examples. These tripeptide derivatives are grouped in the following Table 1.

The dipeptide and tripeptide intermediates used for the preparation of the tripeptide derivatives shown in Table 1 are listed in Tables 2 and 3.

TABLE 1

| Example | End product | Starting products (mmole) | Method (Example) yield % | | Elementary analysis found % | Elementary analysis calc. % | Aminoacid analysis |
|---|---|---|---|---|---|---|---|
| 11 | 2HBr.H—D-CHG—Leu—Arg—pNA $C_{26}H_{44}N_8O_5Br_2$ | 11e (1 mmole) 2N HBr/AcOH | (1f) 88.2 | C H N Br | 43.72 6.31 16.28 22.33 | 44.08 6.26 15.82 22.56 | CHG:Leu:Arg 0.97:1.00:0.98 |
| 12 | 2HBr.H—D-Val—CHA—Arg—pNA $C_{26}H_{44}N_8O_5Br_2$ | 12e (1 mmole) 2N HBr/AcOH | (1f) 86.4 | C H N Br | 43.60 6.41 16.15 22.21 | 44.08 6.26 15.82 22.56 | Val:CHA:Arg 1.00:0.96:1.02 |
| 13 | 2HBr.H—D-Ile—CHA—Arg—pNA $C_{27}H_{46}N_8O_5Br_2$ | 13e (1.5 mmole) 2N HBr/AcOH | (1f) 88.9 | C H N Br | 44.48 6.53 16.09 21.85 | 44.88 6.42 15.51 22.12 | Ile:CHA:Arg 1.00:0.98:0.99 |
| 14 | 2HBr.H—D-Val—CHA—Lys—pNA $C_{26}H_{44}N_6O_5Br_2$ | 14e (0.8 mmole) 2N HBr/AcOH | (2f) 91.0 | C H N Br | 45.30 6.58 12.69 23.17 | 45.89 6.52 12.35 23.49 | Val:CHA:Lys 1.00:1.03:0.99 |
| 15 | 2HBr.H—D-Ile—CHA—Lys—pNA $C_{27}H_{46}N_6O_5Br_2$ | 15e (1.2 mmole) 2N HBr/AcOH | (2f) 90.3 | C H N Br | 46.10 6.75 11.81 22.75 | 46.69 6.68 12.10 23.01 | Ile:CHA:Lys 1.00:0.98:1.02 |
| 16 | 2HBr.H—D-CHG—Phe—Arg—pNA $C_{29}H_{42}N_8O_5Br_2$ | 16e (1 mmole) 2N HBr/AcOH | (1f) 85.6 | C H N Br | 46.22 5.78 14.82 21.33 | 46.91 5.70 15.09 21.52 | CHG:Phe:Arg 0.97:1.00:1.01 |
| 17 | 2HBr.H—D-CHT—Phe—Arg—pNA $C_{30}H_{44}N_8O_6Br_2$ | 17e (1.25 mmole) 2N HBr/AcOH | (1f) 79.4 | C H N Br | 45.95 5.80 14.70 20.55 | 46.64 5.74 14.51 20.69 | CHT:Phe:Arg 0.96:1.00:1.03 |
| 18 | 2HBr.H—D-Ph'Gly—CHA—Arg—pNA $C_{29}H_{42}N_8O_5Br_2$ | 18e (1.1 mmole) 2N HBr/AcOH | (1f) 82.6 | C H N Br | 46.54 5.73 15.25 21.28 | 46.91 5.70 15.09 21.52 | Ph'Gly:CHA:Arg 1.00:0.99:1.00 |
| 19 | 2HBr.H—D-CHA—Pro—Arg—pNA $C_{26}H_{42}N_8O_5Br_2$ | 19e (1 mmole) 2N HBr/AcOH | (1f) 86.4 | C H N Br | 44.15 6.06 16.13 22.44 | 44.20 5.99 15.86 22.62 | CHA:Pro:Arg 0.98:0.99:1.00 |
| 20 | 2HBr.H—D-CHG—CHA—Lys—pNA $C_{29}H_{48}N_6O_5Br_2$ | 20e (1 mmole) 2N HBr/AcOH | (2f) 92.4 | C H N Br | 47.81 6.72 11.59 21.83 | 48.34 6.71 11.66 22.18 | CHG:CHA:Lys 1.02:0.99:1.00 |
| 21 | 2HBr.H—D-CHG—Leu—Lys—pNA $C_{26}H_{44}N_6O_5Br_2$ | 21e (0.9 mmole) 2N HBr/AcOH | (2f) 92.5 | C H N Br | 45.35 6.60 12.67 23.17 | 45.89 6.52 12.35 23.49 | CHG:Leu:Lys 0.99:1.00:1.02 |
| 22 | 2HBr.H—D-Pro—CHA—Arg—pNA $C_{26}H_{42}N_8O_5Br_2$ | 22e (1.1 mmole) 2N HBr/AcOH | (1f) 88.8 | C H N Br | 43.74 6.08 16.16 22.41 | 44.20 5.99 15.86 22.62 | Pro:CHA:Arg 0.98:1.01:1.00 |
| 23 | 2HBr.H—D-CHT—Pro—Arg—pNA $C_{26}H_{42}N_8O_6Br_2$ | 23e (0.75 mmole) 2N HBr/AcOH | (1f) 82.4 | C H N Br | 43.05 5.96 15.70 21.88 | 43.22 5.86 15.51 22.12 | CHT:Pro:Arg 1.00:1.02:1.00 |
| 24 | 2HBr.H—D-Pro—CHG—Arg—pNA $C_{25}H_{40}N_8O_5Br_2$ | 24e (1 mmole) 2N HBr/AcOH | (1f) 85.4 | C H N Br | 42.94 5.91 16.34 22.75 | 43.36 5.82 16.18 23.08 | Pro:CHG:Arg 0.98:0.97:1.00 |
| 25 | 2HBr.H—D-Pro—CHT—Arg—pNA $C_{26}H_{42}N_8O_6Br_2$ | 25e (0.9 mmole) 2N HBr/AcOH | (1f) 76.8 | C H | 42.85 5.96 | 43.22 5.86 | Pro:CHT:Arg 1.01:0.96:1.00 |

TABLE 1-continued

| Example | End product | Starting products (mmole) | Method (Example) yield % | | Elementary analysis found % | calc. % | Aminoacid analysis |
|---|---|---|---|---|---|---|---|
| | | | | N | 15.86 | 15.51 | |
| | | | | Br | 21.84 | 22.12 | |
| 26 | 2HBr.H—D-Ph'Gly—Leu—Arg—pNA $C_{26}H_{38}N_8O_5Br_2$ | 26e (0.8 mmole) 2N HBr/AcOH | (1f) 79.5 | C H N Br | 43.60 5.44 16.06 22.17 | 43.71 5.36 15.68 22.37 | Ph'Gly:Leu:Arg 0.99:1.00:0.99 |
| 27 | 2HBr.H—D-CHG—Pro—Arg—pNA $C_{25}H_{40}N_8O_5Br_2$ | 27e (1.2 mmole) 2N HBr/AcOH | (1f) 84.8 | C H N Br | 42.80 5.92 16.44 22.70 | 43.36 5.82 16.18 23.08 | CHG:Pro:Arg 1.01:1.02:1.00 |
| 28 | 2HBr.H—D-CHT—Pip—Arg—pNA $C_{27}H_{44}N_8O_6Br_2$ | 28e (0.65 mmole) 2N HBr/AcOH | (1f) 82.6 | C H N Br | 43.96 6.09 15.77 21.53 | 44.03 6.02 15.22 21.70 | CHT:Pip:Arg 0.99:0.96:1.00 |
| 29 | 2AcOH.H—D-CHA—Pro—Lys—pNA $C_{30}H_{48}N_6O_9$ | 29e (0.75 mmole) 2N HBr/AcOH | (2f) 87.5 | C H N | 56.09 7.65 13.48 | 56.59 7.60 13.20 | CHA:Pro:Lys 0.99:0.98:1.00 |
| 30 | 2AcOH.H—D-Val—CHG—Lys—pNA $C_{29}H_{48}N_6O_9$ | 30e (0.75 mmole) 2N HBr/AcOH | (2f) 88.8 | C H N | 56.02 7.82 13.59 | 55.75 7.74 13.45 | Val:CHG:Lys 1.00:0.98:1.01 |
| 31 | 2AcOH.H—D-CHG—Pro—Lys—pNA $C_{29}H_{46}N_6O_9$ | 31e (0.75 mmole) 2N HBr/AcOH | (2f) 85.4 | C H N | 55.49 7.55 13.78 | 55.93 7.45 13.50 | CHG:Pro:Lys 0.97:0.99:1.00 |
| 32 | 2AcOH.H—D-CHT—Pro—Lys—pNA $C_{30}H_{48}N_6O_{10}$ | 32e (0.75 mmole) 2N HBr/AcOH | (2f) 79.8 | C H N | 55.01 7.44 13.18 | 55.20 7.41 12.88 | CHT:Pro:Lys 0.96:0.99:1.00 |
| 33 | 2AcOH.H—D-Ph'Gly—CHA—Lys—pNA $C_{33}H_{48}N_6O_9$ | 33e (0.75 mmole) 2N HBr/AcOH | (2f) 75.5 | C H N | 59.25 7.18 12.66 | 58.91 7.19 12.49 | Ph'Gly:CHA:Lys 0.99:0.98:1.00 |
| 34 | 2AcOH.H—D-Val—CHT—Lys—pNA $C_{30}H_{50}N_6O_{10}$ | 34e (0.75 mmole) 2N HBr/AcOH | (2f) 84.4 | C H N | 54.90 7.78 13.05 | 55.03 7.70 12.84 | Val:CHT:Lys 1.00:0.98:1.01 |
| 35 | 2AcOH.H—D-Ph'Gly—CHT—Lys—pNA $C_{33}H_{48}N_6O_{10}$ | 35e (0.75 mmole) 2N HBr/AcOH | (2f) 73.8 | C H N | 57.18 7.09 12.40 | 57.54 7.02 12.20 | Ph'Gly:CHT:Lys 0.98:0.96:1.00 |
| 36 | 2HBr.H—D-Leu—CHA—Arg—pNA $C_{27}H_{46}N_8O_5Br_2$ | 36e (1 mmole) 2N HBr/AcOH | (1f) 85.2 | C H N Br | 44.55 6.53 15.85 21.92 | 44.88 6.42 15.51 22.12 | Leu:CHA:Arg 1.00:0.98:0.99 |
| 37 | 2HBr.H—D-Nleu—CHA—Arg—pNA $C_{27}N_{46}N_8O_5Br_2$ | 37e (1 mmole) 2N HBr/AcOH | (1f) 86.0 | C H N Br | 44.75 6.49 15.79 21.82 | 44.88 6.42 15.51 22.12 | Nleu:CHA:Arg 1.00:0.97:0.99 |
| 38 | 2HBr.H—D-Nval—CHA—Arg—pNA $C_{26}H_{44}N_8O_5Br_2$ | 38e (1 mmole) 2N HBr/AcOH | (1f) 87.1 | C H N Br | 44.39 6.28 16.09 22.33 | 44.08 6.26 15.82 22.56 | Nval:CHA:Arg 1.00:0.98:0.98 |
| 39 | 2HBr.H—D-Phe—CHA—Arg—pNA $C_{30}H_{44}N_8O_5Br_2$ | 39e (1 mmole) 2N HBr/AcOH | (1f) 82.3 | C H N Br | 47.47 5.92 15.08 20.85 | 47.63 5.86 14.81 21.12 | Phe:CHA:Arg 1.00:0.98:1.01 |
| 40 | 2HBr.H—D-Ala—CHA—Arg—pNA $C_{24}H_{40}N_8O_5Br_2$ | 40e (1 mmole) 2N HBr/AcOH | (1f) 86.0 | C H N Br | 41.97 5.92 16.59 23.11 | 42.36 5.93 16.47 23.49 | Ala:CHA:Arg 1.00:0.97:0.99 |
| 41 | 2HBr.H—D-But—CHA—Arg—pNA $C_{25}H_{42}N_8O_5Br_2$ | 41e (1 mmole) 2N HBr/AcOH | (1f) 81.9 | C H N Br | 43.18 6.16 16.27 22.73 | 43.24 6.10 16.14 23.01 | But:CHA:Arg 1.00:0.98:1.01 |
| 42 | 2HBr.H—D-CHG—Tyr—Arg—pNA $C_{29}H_{42}N_8O_6Br_2$ | 42e (0.5 mmole) 2N HBr/AcOH | (1f) 77.8 | C H N Br | 45.77 5.64 15.01 20.84 | 45.92 5.58 14.77 21.07 | CHG:Tyr:Arg 0.97:1.00:0.99 |
| 43 | 2HBr.H—D-CHA—Tyr—Arg—pNA $C_{30}H_{44}N_8O_6Br_2$ | 43e (0.5 mmole) 2N HBr/AcOH | (1f) 72.1 | C H N Br | 46.39 5.73 14.60 20.50 | 46.64 5.74 14.51 20.69 | CHA:Tyr:Arg 0.98:1.00:1.00 |
| 44 | 2HBr.H—D-Nval—Tyr—Arg—pNA $C_{26}H_{38}N_8O_6Br_2$ | 44e (0.5 mmole) 2N HBr/AcOH | (1f) 70.5 | C H N Br | 43.29 5.31 15.82 22.07 | 43.47 5.33 15.60 22.24 | Nval:Tyr:Arg 1.02:1.00:0.98 |
| 45 | 2HBr.H—D-CHT—Tyr—Arg—pNA $C_{30}H_{44}N_8O_7Br_2$ | 45e (0.5 mmole) 2N HBr/AcOH | (1f) 69.9 | C H N Br | 45.20 5.68 14.39 20.05 | 45.69 5.62 14.21 20.27 | CHT:Tyr:Arg 0.96:1.00:0.99 |
| 46 | 2HBr.H—D-Phe—Tyr—Arg—pNA $C_{30}H_{38}N_8O_6Br_2$ | 46e (0.5 mmole) 2N HBr/AcOH | (1f) 73.0 | C H N | 47.51 5.07 14.88 | 47.01 5.00 14.62 | Phe:Tyr:Arg 1.00:1.01:0.98 |

TABLE 1-continued

| Example | End product | Starting products (mmole) | Method (Example) yield % | | Elementary analysis found % | Elementary analysis calc. % | Aminoacid analysis |
|---|---|---|---|---|---|---|---|
| | | | | Br | 20.46 | 20.85 | |
| 47 | 2HBr.H—D-Ph'Gly—Tyr—Arg—pNA $C_{29}H_{36}N_8O_6Br_2$ | 47e (0.5 mmole) 2N HBr/AcOH | (1f) 67.8 | C H N | 46.57 4.90 15.13 | 46.30 4.82 14.89 | Ph'Gly:Tyr:Arg 0.97:1.00:0.99 |
| | | | | Br | 20.98 | 21.24 | |
| 48 | 2HBr.H—D-CHG—Ala—Arg—pNA $C_{23}H_{38}N_8O_5Br_2$ | 48e (1 mmole) 2N HBr/AcOH | (1f) 83.4 | C H N | 41.66 5.74 17.09 | 41.45 5.75 16.82 | CHG:Ala:Arg 0.96:1.00:0.99 |
| | | | | Br | 23.90 | 23.98 | |
| 49 | 2HBr.H—D-CHA—Ala—Arg—pNA $C_{24}H_{40}N_8O_5Br_2$ | 49e (1 mmole) 2N HBr/AcOH | (1f) 88.1 | C H N | 42.54 5.98 16.60 | 42.36 5.93 16.47 | CHA:Ala:Arg 0.98:1.00:1.00 |
| | | | | Br | 23.19 | 23.49 | |
| 50 | 2HBr.H—D-Phe—Leu—Arg—pNA $C_{27}H_{40}N_8O_5Br_2$ | 50e (1 mmole) 2N HBr/AcOH | (1f) 84.4 | C H N | 45.49 5.66 15.69 | 45.26 5.63 15.64 | Phe:Leu:Arg 1.01:1.00:0.99 |
| | | | | Br | 22.03 | 22.31 | |
| 51 | 2HBr.H—D-CHT—Leu—Arg—pNA $C_{27}H_{46}N_8O_6Br_2$ | 51e (1 mmole) 2N HBr/AcOH | (1f) 80.7 | C H N | 43.80 6.33 15.42 | 43.91 6.28 15.17 | CHT:Leu:Arg 0.96:1.00:0.99 |
| | | | | Br | 21.37 | 21.64 | |
| 52 | 2HBr.H—D-CHA—Leu—Arg—pNA $C_{27}H_{46}N_8O_5Br_2$ | 52e (1 mmole) 2N HBr/AcOH | (1f) 84.5 | C H N | 44.38 6.41 15.75 | 44.88 6.42 15.51 | CHA:Leu:Arg 0.97:1.00:1.01 |
| | | | | Br | 21.85 | 22.12 | |
| 53 | 2HBr.H—D-Leu—Ph'Gly—Arg—pNA $C_{26}H_{38}N_8O_5Br_2$ | 53e (0.5 mmole) 2N HBr/AcOH | (1f) 82.3 | C H N | 44.18 5.50 16.18 | 44.46 5.45 15.95 | Leu:Ph'Gly:Arg 1.00:0.97:0.98 |
| | | | | Br | 22.48 | 22.75 | |
| 54 | 2HBr.H—D-Nval—Ph'Gly—Arg—pNA $C_{25}H_{36}N_8O_5Br_2$ | 54e (0.5 mmole) 2N HBr/AcOH | (1f) 79.8 | C H N | 43.24 5.33 16.39 | 43.62 5.27 16.28 | Nval:Ph'Gly:Arg 1.00:0.98:1.01 |
| | | | | Br | 22.87 | 23.21 | |
| 55 | 2HBr.H—D-Ala—Ph'Gly—Arg—pNA $C_{23}H_{32}N_8O_5Br_2$ | 55e (0.5 mmole) 2N HBr/AcOH | (1f) 82.1 | C H N | 41.46 4.93 17.19 | 41.83 4.88 16.97 | Ala:Ph'Gly:Arg 1.00:0.98:0.99 |
| | | | | Br | 23.92 | 24.20 | |
| 56 | 2HBr.H—D-CHA—Ph'Gly—Arg—pNA $C_{29}H_{42}N_8O_5Br_2$ | 56e (0.5 mmole) 2N HBr/AcOH | (1f) 77.6 | C H N | 46.75 5.73 15.40 | 46.91 5.70 15.09 | CHA:Ph'Gly:Arg 0.97:0.98:1.00 |
| | | | | Br | 21.22 | 21.52 | |
| 57 | 2HBr.H—D-CHT—Ph'Gly—Arg—pNA $C_{29}H_{42}N_8O_6Br_2$ | 57e (0.5 mmole) 2N HBr/AcOH | (1f) 76.4 | C H N | 45.64 5.61 15.00 | 45.92 5.58 14.77 | CHT:Ph'Gly:Arg 0.96:0.99:1.00 |
| | | | | Br | 20.69 | 21.07 | |
| 58 | 2HBr.H—D-CHG—Ph'Gly—Arg—pNA $C_{28}H_{40}N_8O_5Br_2$ | 58e (0.5 mmole) 2N HBr/AcOH | (1f) 75.9 | C H N | 46.02 5.59 15.67 | 46.16 5.53 15.38 | CHG:Ph'Gly:Arg 0.98:0.98:1.00 |
| | | | | Br | 21.48 | 21.94 | |
| 59 | 2HBr.H—D-CHG—CHG—Arg—pNA $C_{28}H_{46}N_8O_5Br_2$ | 59e (1 mmole) 2N HBr/AcOH | (1f) 84.6 | C H N | 45.65 6.38 15.44 | 45.78 6.31 15.26 | CHG:Arg 1.93:1.00 |
| | | | | Br | 21.52 | 21.76 | |
| 60 | 2HBr.H—D-Pip—CHG—Arg—pNA $C_{26}H_{42}N_8O_5Br_2$ | 60e (1 mmole) 2N HBr/AcOH | (1f) 80.1 | C H N | 43.91 6.05 16.18 | 44.20 5.99 15.86 | Pip:CHG:Arg 0.97:0.99:1.00 |
| | | | | Br | 22.47 | 22.62 | |
| 61 | 2HBr.H—D-Phe—CHG—Arg—pNA $C_{29}H_{42}N_8O_5Br_2$ | 61e (1 mmole) 2N HBr/AcOH | (1f) 88.4 | C H N | 46.70 5.68 15.27 | 46.91 5.70 15.09 | Phe:CHG:Arg 1.00:0.98:1.01 |
| | | | | Br | 21.33 | 21.52 | |
| 62 | 2HBr.H—D-Ph'Gly—CHG—Arg—pNA $C_{28}H_{40}N_8O_5Br_2$ | 62e (1 mmole) 2N HBr/AcOH | (1f) 82.7 | C H N | 46.18 5.60 15.62 | 46.16 5.53 15.38 | Ph'Gly:CHG:Arg 0.98:0.98:1.00 |
| | | | | Br | 21.77 | 21.94 | |
| 63 | 2HBr.H—D-Ph'Gly—Phe—Arg—pNA $C_{29}H_{36}N_8O_5Br_2$ | 63e (0.5 mmole) 2N HBr/AcOH | (1f) 80.0 | C H N | 47.08 5.00 15.38 | 47.29 4.93 15.22 | Ph'Gly:Phe:Arg 0.97:1.00:0.99 |
| | | | | Br | 21.61 | 21.70 | |
| 64 | 2HBr.H—D-CHA—Phe—Arg—pNA $C_{30}H_{44}N_8O_5Br_2$ | 64e (0.5 mmole) 2N HBr/AcOH | (1f) 82.5 | C H N | 47.32 5.84 14.90 | 47.63 5.86 14.81 | CHA:Phe:Arg 0.96:1.00:0.99 |
| | | | | Br | 20.88 | 21.12 | |
| 65 | 2HBr.H—D-CHG—Pip—Arg—pNA $C_{26}H_{42}N_8O_5Br_2$ | 65e (0.5 mmole) 2N HBr/AcOH | (1f) 77.7 | C H N | 43.87 6.04 16.18 | 44.20 5.99 15.86 | CHG:Pip:Arg 0.98:0.96:1.00 |
| | | | | Br | 22.40 | 22.62 | |
| 66 | 2HBr.H—D-CHA—Pip—Arg—pNA | 66e (0.5 mmole) | (1f) | C | 44.76 | 45.01 | CHA:Pip:Arg |

TABLE 1-continued

| Example | End product | Starting products (mmole) | Method (Example) yield % | | Elementary analysis found % | Elementary analysis calc. % | Aminoacid analysis |
|---|---|---|---|---|---|---|---|
| | $C_{27}H_{44}N_8O_5Br_2$ | 2N HBr/AcOH | 76.9 | H | 6.18 | 6.16 | 0.98:0.95:1.00 |
| | | | | N | 15.73 | 15.55 | |
| | | | | Br | 22.01 | 22.18 | |
| 67 | 2HBr.H—D-CHG—Nleu—Arg—pNA | 67e (1 mmole) | (1f) | C | 43.68 | 44.08 | CHG:Nleu:Arg |
| | $C_{26}H_{44}N_8O_5Br_2$ | 2N HBr/AcOH | 85.8 | H | 6.30 | 6.26 | 0.97:1.00:0.99 |
| | | | | N | 16.02 | 15.82 | |
| | | | | Br | 22.33 | 22.56 | |
| 68 | 2HBr.H—D-CHA—Nleu—Arg—pNA | 68e (1 mmole) | (1f) | C | 44.59 | 44.88 | CHA:Nleu:Arg |
| | $C_{27}H_{46}N_8O_5Br_2$ | 2N HBr/AcOH | 87.4 | H | 6.45 | 6.42 | 0.98:1.00:0.98 |
| | | | | N | 15.62 | 15.51 | |
| | | | | Br | 21.87 | 22.12 | |
| 69 | 2HBr.H—D-CHA—Nval—Arg—pNA | 69e (0.5 mmole) | (1f) | C | 43.90 | 44.08 | CHA:Nval:Arg |
| | $C_{26}H_{44}N_8O_5Br_2$ | 2N HBr/AcOH | 90.2 | H | 6.32 | 6.26 | 0.97:1.00:0.99 |
| | | | | N | 16.18 | 15.82 | |
| | | | | Br | 22.39 | 22.56 | |
| 70 | 2HBr.H—D-CHG—Nval—Arg—pNA | 70e (0.5 mmole) | (1f) | C | 43.20 | 43.24 | CHG:Nval:Arg |
| | $C_{25}H_{42}N_8O_5Br_2$ | 2N HBr/AcOH | 88.5 | H | 6.15 | 6.10 | 0.96:1.00:1.01 |
| | | | | N | 16.36 | 16.14 | |
| | | | | Br | 22.78 | 23.01 | |
| 71 | 2HBr.H—D-Nval—CHA—Lys—pNA | 71c (1 mmole) | (2f) | C | 45.73 | 45.89 | Nval:CHA:Arg |
| | $C_{26}H_{44}N_6O_5Br_2$ | 2N HBr/AcOH | 76.4 | H | 6.61 | 6.52 | 1.00:0.98:0.99 |
| | | | | N | 12.48 | 12.35 | |
| | | | | Br | 23.18 | 23.49 | |
| 72 | 2HBr.H—D-But—CHA—Lys—pNA | 72e (1 mmole) | (2f) | C | 44.75 | 45.05 | But:CHA:Lys |
| | $C_{25}H_{42}N_6O_5Br_2$ | 2N HBr/AcOH | 74.6 | H | 6.39 | 6.35 | 1.02:0.98:1.00 |
| | | | | N | 12.67 | 12.61 | |
| | | | | Br | 23.68 | 23.98 | |
| 73 | 2HBr.H—D-Leu—CHA—Lys—pNA | 73e (1 mmole) | (2f) | C | 46.39 | 46.69 | Leu:CHA:Lys |
| | $C_{27}H_{46}N_6O_5Br_2$ | 2N HBr/AcOH | 78.0 | H | 6.63 | 6.68 | 1.00:0.97:1.01 |
| | | | | N | 12.27 | 12.10 | |
| | | | | Br | 22.81 | 23.01 | |
| 74 | 2HBr.H—D-Nleu—CHA—Lys—pNA | 74e (1 mmole) | (2f) | C | 46.88 | 46.69 | Nleu:CHA:Lys |
| | $C_{27}H_{46}N_6O_5Br_2$ | 2N HBr/AcOH | 77.6 | H | 6.72 | 6.68 | 0.99:0.97:1.00 |
| | | | | N | 12.33 | 12.10 | |
| | | | | Br | 22.75 | 23.01 | |
| 75 | 2HBr.H—D-CHG—But—Arg—pNA | 75e (1 mmole) | (1f) | C | 42.18 | 42.36 | CHG:But:Arg |
| | $C_{24}H_{40}N_8O_5Br_2$ | 2N HBr/AcOH | 84.7 | H | 6.00 | 5.93 | 0.97:0.99:1.00 |
| | | | | N | 16.52 | 16.47 | |
| | | | | Br | 23.18 | 23.49 | |
| 76 | 2HBr.H—D-CHA—But—Arg—pNA | 76e (1 mmole) | (1f) | C | 42.96 | 43.24 | CHA:But:Arg |
| | $C_{25}H_{42}N_8O_5Br_2$ | 2N HBr/AcOH | 88.5 | H | 6.12 | 6.10 | 0.98:0.98:1.00 |
| | | | | N | 16.25 | 16.14 | |
| | | | | Br | 22.69 | 23.01 | |
| 77 | 2HBr.H—D-CHT—But—Arg—pNA | 77e (1 mmole) | (1f) | C | 41.89 | 42.26 | CHT:But:Arg |
| | $C_{25}H_{42}N_8O_6Br_2$ | 2N HBr/AcOH | 82.3 | H | 6.01 | 5.96 | 0.96:0.99:1.00 |
| | | | | N | 15.96 | 15.77 | |
| | | | | Br | 22.15 | 22.49 | |

TABLE 2

| Example | Dipeptide precursor | Starting products (mmole) | Method (Example) yield % | | Elementary analysis found % | Elementary analysis calc. % |
|---|---|---|---|---|---|---|
| 11c | Cbo—Leu—Arg—pNA.HBr | 1b (5 mmole) | (1c) | C | 50.75 | 50.16 |
| | $C_{26}H_{36}N_7O_6Br$ | Cbo—LeuOpNP | 82.4 | H | 5.95 | 5.83 |
| | | (5.5 mmole) | | N | 16.10 | 15.75 |
| | | | | Br | 12.69 | 12.84 |
| 11d | 2HBr.H.Leu—Arg—pNA | 11c (3 mmole) | (1d) | C | 38.42 | 37.98 |
| | $C_{18}H_{31}N_7O_4Br_2$ | 2N HBr/AcOH | 90.3 | H | 5.55 | 5.49 |
| | | | | N | 17.84 | 17.23 |
| | | | | Br | 27.67 | 28.07 |
| 14c | BOC—CHA—Lys(ε-Cbo)—pNA | 2b (5 mmole) | (2c) | C | 63.05 | 62.46 |
| | $C_{34}H_{47}N_5O_8$ | BOC—CHA—OpNP | 84.2 | H | 7.35 | 7.25 |
| | | (5.5 mmole) | | N | 10.98 | 10.71 |
| 14d | $CF_3COOH.H$—CHA—Lys(ε-Cbo)—pNA | 14c (3 mmole) | (2d) | C | 56.08 | 55.77 |
| | $C_{31}H_{40}N_5O_8F_3$ | 6ml $CF_3COOH$ | 91.6 | H | 6.15 | 6.04 |
| | | | | N | 11.01 | 10.49 |
| 16c | Cbo—Phe—Arg—pNA.HBr | 1b (5 mmole) | (1c) | C | 53.45 | 53.05 |
| | $C_{29}H_{34}N_7O_6Br$ | Cbo—Phe—OpNP | 84.8 | H | 5.30 | 5.22 |
| | | (5.5 mmole) | | N | 15.15 | 14.94 |
| | | | | Br | 11.95 | 12.17 |
| 16d | 2HBr.H—Phe—Arg—pNA | 16c (3 mmole) | (1d) | C | 41.38 | 41.81 |
| | $C_{21}H_{29}N_7O_4Br_2$ | 2N HBr/AcOH | 93.5 | H | 4.78 | 4.85 |
| | | | | N | 16.50 | 16.25 |
| | | | | Br | 26.15 | 26.49 |
| 19e | Cbo—Pro—Arg—pNA.HBr | 1b (5 mmole) | (1c) | C | 49.95 | 49.51 |

TABLE 2-continued

| Example | Dipeptide precursor | Starting products (mmole) | Method (Example) yield % | | Elementary analysis found % | calc. % |
|---|---|---|---|---|---|---|
| | $C_{25}H_{32}N_7O_6Br$ | Cbo—Pro—OpNP (5.5 mmole) | 88.1 | H N Br | 5.40 16.19 12.82 | 5.32 16.17 13.17 |
| 19d | 2HBr.H—Pro—Arg—pNA $C_{17}H_{27}N_7O_4Br_2$ | 19c (3 mmole) 2N HBr/AcOH | (1d) 92.0 | C H N Br | 37.41 5.03 18.15 28.50 | 36.91 4.92 17.72 28.88 |
| 21c | BOC—Leu—Lys(ε-Cbo)—pNA $C_{31}H_{43}N_5O_8$ | 2b (5 mmole) BOC—Leu—OpNP (5.5 mmole) | (2c) 87.3 | C H N | 61.10 7.15 11.88 | 60.67 7.06 11.41 |
| 21d | $CF_3COOH.H$—Leu—Lys(ε-Cbo)—pNA $C_{28}H_{36}N_5O_8F_3$ | 21c (3 mmole) 6ml $CF_3COOH$ | (2d) 90.9 | C H N | 53.40 5.85 11.50 | 53.58 5.78 11.16 |
| 24c | Cbo—CHG—Arg—pNA.HBr $C_{28}H_{38}N_7O_6Br$ | 1b (5 mmole) Cbo—CHG—OpNP (5.5 mmole) | (1c) 79.6 | C H N Br | 52.20 6.09 15.55 12.05 | 51.85 5.91 15.12 12.32 |
| 24d | 2HBr.H—CHG—Arg—pNA $C_{20}H_{33}N_7O_4Br_2$ | 24c (3 mmole) 2N HBr/AcOH | (1d) 88.4 | C H N Br | 40.95 5.53 17.06 26.58 | 40.35 5.59 16.47 26.84 |
| 25c | Cbo—CHT—Arg—pNA.HBr $C_{29}H_{40}N_7O_7Br$ | 1b (5 mmole) Cbo—CHT—OpNP (5.5 mmole) | (1c) 75.7 | C H N Br | 52.08 6.04 14.90 11.60 | 51.33 5.94 14.45 11.76 |
| 25d | 2HBr.H—CHT—Arg—pNA $C_{21}H_{35}N_7O_5Br_2$ | 25c (2.5 mmole) 2N HBr/AcOH | (1d) 88.9 | C H N Br | 40.87 5.56 16.18 25.22 | 40.33 5.64 15.68 25.55 |
| 28c | Cbo—Pip—Arg—pNA.HBr $C_{26}H_{34}N_7O_6Br$ | 1b (5 mmole) Cbo—Pip—OpNP (5.5 mmole) | (1c) 82.3 | C H N Br | 50.80 5.50 16.19 12.66 | 50.33 5.52 15.80 12.88 |
| 28d | 2HBr.H—Pip—Arg—pNA $C_{18}H_{29}N_7O_4Br_2$ | 28c (2.5 mmole) 2N HBr/AcOH | (1d) 91.0 | C H N Br | 38.49 5.14 17.90 27.86 | 38.11 5.15 17.28 28.17 |
| 29c | BOC—Pro—Lys(ε-Cbo)—pNA $C_{30}H_{39}N_5O_8$ | 2b (5 mmole) BOC—Pro—OpNP (5.5 mmole) | (2c) 88.5 | C H N | 59.82 6.65 11.94 | 60.29 6.58 11.72 |
| 29d | $CF_3COOH.H$—Pro—Lys(ε-Cbo)—pNA $C_{27}H_{32}N_5O_8F_3$ | 29c (3 mmole) 6ml $CF_3COOH$ | (2d) 93.0 | C H N | 52.91 5.32 11.66 | 53.03 5.27 11.45 |
| 30c | BOC—CHG—Lys(ε-Cbo)—pNA $C_{33}H_{45}N_5O_8$ | 2b (5 mmole) BOC—CHG—OpNP (5.5 mmole) | (2c) 84.6 | C H N | 61.50 7.08 11.18 | 61.95 7.09 10.95 |
| 30d | $CF_3COOH.H$—CHG—Lys(ε-Cbo)—pNA $C_{30}H_{38}N_5O_8F_3$ | 30c (3 mmole) 6ml $CF_3COOH$ | (2d) 90.5 | C H N | 54.75 5.93 11.08 | 55.12 5.86 10.71 |
| 34c | BOC—CHT—Lys(ε-Cbo)—pNA $C_{34}H_{47}N_5O_9$ | 2b (5 mmole) BOC—CHT—OpNP (5.5 mmole) | (2c) 84.3 | C H N | 60.48 7.11 10.76 | 60.97 7.07 10.46 |
| 34d | $CF_3COOH.H$—CHT—Lys(ε-Cbo)—pNA $C_{31}H_{40}N_5O_9F_3$ | 34c (3 mmole) 6ml $CF_3COOH$ | (2d) 90.8 | C H N | 54.08 6.00 10.18 | 54.46 5.90 10.24 |
| 42c | Cbo—Tyr(OBzl)—Arg—pNA.HBr $C_{36}H_{40}N_7O_7Br$ | 1b (5 mmole) Cbo—Tyr(OBzl)—OpNP (5.5 mmole) | (1c) 77.6 | C H N Br | 56.08 5.35 12.95 10.15 | 56.69 5.29 12.86 10.48 |
| 42d | 2HBr.H—Tyr—Arg—pNA $C_{21}H_{29}N_7O_5Br_2$ | 42c (5 mmole) 2N HBr/AcOH | (1d) 83.7 | C H N Br | 40.63 4.77 16.08 25.38 | 40.73 4.72 15.83 25.80 |
| 48c | Cbo—Ala—Arg—pNA.HBr $C_{23}H_{30}N_7O_6Br$ | 1b (5 mmole) Cbo—Ala—OpNP (5.5 mmole) | (1c) 88.5 | C H N Br | 47.19 5.22 17.18 13.60 | 47.59 5.21 16.89 13.77 |
| 48d | 2HBr.H—Ala—Arg—pNA $C_{15}H_{25}N_7O_4Br_2$ | 48c (3 mmole) 2N HBr/AcOH | (1d) 90.8 | C H N Br | 34.01 4.76 18.85 29.88 | 34.17 4.78 18.60 30.31 |
| 53c | Cbo—Ph'Gly—Arg—pNA.HBr $C_{28}H_{32}N_7O_6Br$ | 1b (5 mmole) Cbo—Ph'Gly—OpNP (5.5 mmole) | (1c) 86.7 | C H N Br | 52.00 4.99 15.17 12.23 | 52.34 5.02 15.26 12.44 |
| 53d | 2HBr.H—Ph'Gly—Arg—pNA $C_{20}H_{27}N_7O_4Br_2$ | 53c (3 mmole) 2N HBr/AcOH | (1d) 93.4 | C H N Br | 40.38 4.66 16.92 26.84 | 40.76 4.62 16.64 27.12 |

TABLE 2-continued

| Example | Dipeptide precursor | Starting products (mmole) | Method (Example) yield % | | Elementary analysis found % | calc. % |
|---|---|---|---|---|---|---|
| 67c | Cbo—Nleu—Arg—pNA.HBr<br>C₂₆H₃₆N₇O₆Br | 1b (5 mmole)<br>Cbo—Nleu—OpNP<br>(5.5 mmole) | (1c)<br>90.0 | C<br>H<br>N<br>Br | 49.82<br>5.88<br>16.03<br>12.62 | 50.16<br>5.83<br>15.75<br>12.84 |
| 67d | 2HBr.H—Nleu—Arg—pNA<br>C₂₈H₃₁N₇O₄Br₂ | 67c (3 mmole)<br>2N HBr/AcOH | (1d)<br>94.6 | C<br>H<br>N<br>Br | 48.52<br>4.57<br>14.50<br>22.91 | 48.78<br>4.53<br>14.22<br>23.18 |
| 69c | Cbo—Nval—Arg—pNA.HBr<br>C₂₅H₃₄N₇O₆Br | 1b (5 mmole)<br>Cbo—Nval—OpNP<br>(5.5 mmole) | (1c)<br>90.8 | C<br>H<br>N<br>Br | 49.13<br>5.69<br>16.38<br>13.00 | 49.35<br>5.63<br>16.11<br>13.13 |
| 69d | 2HBr.H—Nval—Arg—pNA<br>C₁₇H₂₉N₇O₄Br₂ | 69c (3 mmole)<br>2N HBr/AcOH | (1d)<br>96.0 | C<br>H<br>N<br>Br | 36.45<br>5.30<br>18.01<br>28.55 | 36.77<br>5.26<br>17.66<br>28.78 |
| 75c | Cbo—But—Arg—pNA.HBr<br>C₂₄H₃₂N₇O₆Br | 1b (5 mmole)<br>Cbo—But—OpNP<br>(5.5 mmole) | (1c)<br>91.6 | C<br>H<br>N<br>Br | 48.09<br>5.46<br>16.83<br>13.22 | 48.49<br>5.43<br>16.49<br>13.44 |
| 75d | 2HBr.H—But—Arg—pNA<br>C₁₆H₂₇N₇O₄Br₂ | 75c (3 mmole)<br>2N HBr/AcOH | (1d)<br>94.2 | C<br>H<br>N<br>Br | 35.50<br>5.08<br>18.40<br>29.08 | 35.51<br>5.03<br>18.12<br>29.53 |

TABLE 3

| Example | Tripeptide precursor | Starting products (mmole) | Method (Example) yield % | | Elementary analysis found % | calc. % |
|---|---|---|---|---|---|---|
| 11e | Cbo—D-CHG—Leu—Arg—pNA.HBr<br>C₃₄H₄₉N₈O₇Br | 11d (2 mmole)<br>Cbo—D-CHG—OpNP<br>(2.2 mmole) | (1e)<br>78.6 | C<br>H<br>N<br>Br | 53.04<br>6.49<br>15.15<br>10.22 | 53.67<br>6.48<br>14.71<br>10.49 |
| 12e | Cbo—D-Val—CHA—Arg—pNA.HBr<br>C₃₄H₄₉N₈O₇Br | 1d (2 mmole)<br>Cbo—D-Val—OpNP<br>(2.2 mmole) | (1e)<br>82.7 | C<br>H<br>N<br>Br | 52.88<br>6.54<br>15.03<br>10.25 | 53.61<br>6.48<br>14.71<br>10.49 |
| 13e | Cbo—D-Ile—CHA—Arg—pNA.HBr<br>C₃₅H₅₁N₈O₇Br | 1d (2 mmole)<br>Cbo—D-Ile—OpNP<br>(2.2 mmole) | (1e)<br>83.3 | C<br>H<br>N<br>Br | 53.80<br>6.64<br>14.75<br>10.11 | 54.19<br>6.63<br>14.45<br>10.30 |
| 14e | Cbo—D-Val—CHA—Lys(ε-Cbo)—pNA<br>C₄₂H₅₄N₆O₉ | 14d (2 mmole)<br>Cbo—D-Val—OpNP<br>(2.2 mmole) | (2e)<br>85.8 | C<br>H<br>N | 63.74<br>7.09<br>10.93 | 64.10<br>6.92<br>10.68 |
| 15e | Cbo—D-Ile—CHA—Lys(ε-Cbo)—pNA<br>C₄₃H₅₆N₆O₉ | 14d (2 mmole)<br>Cbo—D-Ile—OpNP<br>(2.2 mmole) | (2e)<br>86.9 | C<br>H<br>N | 64.11<br>7.13<br>10.60 | 64.48<br>7.05<br>10.49 |
| 16e | Cbo—D-CHG—Phe—Arg—pNA.HBr<br>C₃₇H₄₇N₈O₇Br | 16d (1.5 mmole)<br>Cbo—D-CHG—OpNP<br>(1.65 mmole) | (1e)<br>84.1 | C<br>H<br>N<br>Br | 55.21<br>6.01<br>14.23<br>9.85 | 55.85<br>5.95<br>14.08<br>10.04 |
| 17e | Cbo—D-CHT—Phe—Arg—pNA.HBr<br>C₃₈H₄₉N₈O₈Br | 16d (1.5 mmole)<br>(Cbo—D-CHT—OpNP<br>(1.65 mmole) | (1e)<br>81.0 | C<br>H<br>N<br>Br | 54.96<br>5.99<br>13.75<br>9.39 | 55.27<br>5.98<br>13.57<br>9.68 |
| 18e | Cbo—D-Ph'Gly—CHA—Arg—pNA.HBr<br>C₃₇H₄₇N₈O₇Br | 1d (2 mmole)<br>Cbo—D-Ph'Gly—OpNP<br>(2.2 mmole) | (1e)<br>82.7 | C<br>H<br>N<br>Br | 54.86<br>6.04<br>14.38<br>9.81 | 55.85<br>5.95<br>14.08<br>10.04 |
| 19e | Cbo—D-CHA—Pro—Arg—pNA.HBr<br>C₃₄H₄₇N₈O₇Br | 19d (2 mmole)<br>Cbo—D-CHA—OpNP<br>(2.2 mmole) | (1e)<br>80.5 | C<br>H<br>N<br>Br | 53.41<br>6.30<br>15.08<br>10.24 | 53.75<br>6.24<br>14.75<br>10.52 |
| 20e | Cbo—D-CHG—CHA—Lys(ε-Cbo)—pNA<br>C₄₅H₅₈N₆O₉ | 14d (1.5 mmole)<br>Cbo—D-CHG—OpNP<br>(1.65 mmole) | (2e)<br>88.2 | C<br>H<br>N | 64.84<br>7.11<br>10.36 | 65.36<br>7.07<br>10.16 |
| 21e | Cbo—D-CHG—Leu—Lys(ε-Cbo)—pNA<br>C₄₂H₅₄N₆O₉ | 21d (2.5 mmole)<br>Cbo—D-CHG—OpNP<br>(2.75 mmole) | (2e)<br>90.2 | C<br>H<br>N | 63.73<br>7.00<br>10.85 | 64.10<br>6.92<br>10.68 |
| 22e | Cbo—D-Pro—CHA—Arg—pNA.HBr<br>C₃₄H₄₇N₈O₇Br | 1d (2 mmole)<br>Cbo—D-Pro—OpNP<br>(2.2 mmole) | (1e)<br>85.0 | C<br>H<br>N<br>Br | 53.20<br>6.25<br>15.09<br>10.34 | 53.75<br>6.24<br>14.75<br>10.52 |
| 23e | Cbo—D-CHT—Pro—Arg—pNA.HBr<br>C₃₄H₄₇N₈O₈Br | 19d (1.5 mmole)<br>Cbo—D-CHT—OpNP | (1e)<br>83.3 | C<br>H | 51.96<br>5.13 | 52.64<br>6.11 |

TABLE 3-continued

| Example | Tripeptide precursor | Starting products (mmole) | Method (Example) yield % | | Elementary analysis | |
|---|---|---|---|---|---|---|
| | | | | | found % | calc. % |
| | | (1.65 mmole) | | N | 14.87 | 14.45 |
| | | | | Br | 10.09 | 10.30 |
| 24e | Cbo—D-Pro—CHG—Arg—pNA.HBr $C_{33}H_{45}N_8O_7Br$ | 24d (2 mmole) Cbo—D-Pro—OpNP (2.2 mmole) | (1e) 81.4 | C H N Br | 52.91 6.11 15.38 10.40 | 53.15 6.08 15.03 10.72 |
| 25e | Cbo—D-Pro—CHT—Arg—pNA.HBr $C_{34}H_{47}N_8O_8Br$ | 25d (1.5 mmole) Cbo—D-Pro—OpNP (1.65 mmole) | (1e) 78.6 | C H N Br | 51.75 6.09 14.77 10.13 | 52.64 6.11 14.45 10.30 |
| 26e | Cbo—D-Ph'Gly—Leu—Arg—pNA.HBr $C_{34}H_{43}N_8O_7Br$ | 11d (1.5 mmole) Cbo—D-Ph'Gly—OpNP (1.65 mmole) | (1e) 82.4 | C H N Br | 53.44 5.81 15.07 10.47 | 54.04 5.74 14.83 10.57 |
| 27e | Cbo—D-CHG—Pro—Arg—pNA.HBr $C_{33}H_{45}N_8O_7Br$ | 19d (2 mmole) Cbo—D-CHG—OpNP (2.2 mmole) | (1e) 85.5 | C H N Br | 53.04 6.17 15.49 10.45 | 53.15 6.08 15.03 10.72 |
| 28e | Cbo—D-CHT—Pip—Arg—pNA.HBr $C_{35}H_{49}N_8O_8Br$ | 32d (1.5 mmole) Cbo—D-CHT—OpNP (1.65 mmole) | (1e) 78.1 | C H N Br | 52.54 6.27 14.38 9.85 | 53.23 6.25 14.19 10.12 |
| 29e | Cbo—D-CHA—Pro—Lys(ε-Cbo)—pNA $C_{42}H_{52}N_6O_9$ | 29d (2 mmole) Cbo—D-CHA—OpNP (2.2 mmole) | (2e) 82.5 | C H N | 64.54 6.75 10.92 | 64.27 6.68 10.71 |
| 30e | Cbo—D-Val—CHG—Lys(ε-Cbo)—pNA $C_{41}H_{52}N_6O_9$ | 30d (1.5 mmole) Cbo—D-Val—OpNP (1.65 mmole) | (2e) 86.0 | C H N | 63.88 6.79 11.18 | 63.71 6.78 10.87 |
| 31e | Cbo—D-CHG—Pro—Lys(ε-Cbo)—pNA $C_{41}H_{50}N_6O_9$ | 29d (2 mmole) Cbo—D-CHG—OpNP (2.2 mmole) | (2e) 88.4 | C H N | 63.73 6.61 11.18 | 63.88 6.54 10.90 |
| 32e | Cbo—D-CHT—Pro—Lys(ε-Cbo)—pNA $C_{42}H_{52}N_6O_{10}$ | 29d (2 mmole) Cbo—D-CHT—OpNP (2.2 mmole) | (2e) 80.8 | C H N | 62.61 6.58 10.70 | 62.98 6.54 10.49 |
| 33e | Cbo—D-Ph'Gly—CHA—Lys(ε-Cbo)—pNA $C_{45}H_{52}N_6O_9$ | 14d (2 mmole) Cbo—D-Ph'Gly—OpNP (2.2 mmole) | (2e) 76.7 | C H N | 65.59 6.41 10.33 | 65.84 6.38 10.24 |
| 34e | Cbo—D-Val—CHT—Lys(ε-Cbo)—pNA $C_{42}H_{54}N_6O_{10}$ | 34d (1.5 mmole) Cbo—D-Val—OpNP (1.65 mmole) | (2e) 77.9 | C H N | 62.80 6.87 10.61 | 62.83 6.78 10.47 |
| 35e | Cbo—D-Ph'Gly—CHT—Lys(ε-Cbo)—pNA $C_{45}H_{52}N_6O_{10}$ | 34d (1.5 mmole) Cbo—D-Ph'Gly—OpNP (1.65 mmole) | (2e) 75.4 | C H N | 64.40 6.27 10.28 | 64.58 6.26 10.04 |
| 36e | Cbo—D-Leu—CHA—Arg—pNA.HBr $C_{35}H_{51}N_8O_7Br$ | 1d (2 mmole) Cbo—D-Leu—OpNP (2.2 mmole) | (1e) 79.8 | C H N Br | 53.95 6.70 14.66 10.14 | 54.19 6.63 14.45 10.30 |
| 37e | Cbo—D-Nleu—CHA—Arg—pNA.HBr $C_{35}H_{51}N_8O_7Br$ | 1d (2 mmole) Cbo—D-Nleu—OpNP (2.2 mmole) | (1e) 80.4 | C H N Br | 54.08 6.73 14.58 10.08 | 54.19 6.63 14.45 10.30 |
| 38e | Cbo—D-Nval—CHA—Arg—pNA.HBr $C_{34}H_{49}N_8O_7Br$ | 1d (2 mmole) Cbo—D-Nval—OpNP (2.2 mmole) | (1e) 82.6 | C H N Br | 53.28 6.55 14.93 10.25 | 53.61 6.48 14.71 10.49 |
| 39e | Cbo—D-Phe—CHA—Arg—pNA.HBr $C_{38}H_{49}N_8O_7Br$ | 1d (2 mmole) Cbo—D-Phe—OpNP (2.2 mmole) | (1e) 84.5 | C H N Br | 56.23 6.18 14.10 9.75 | 56.36 6.10 13.84 9.87 |
| 40e | Cbo—D-Ala—CHA—Arg—pNA.HBr $C_{32}H_{45}N_8O_7Br$ | 1d (2 mmole) Cbo—D-Ala—OpNP (2.2 mmole) | (1e) 88.2 | C H N Br | 52.01 6.19 15.44 10.62 | 52.39 6.18 15.27 10.89 |
| 41e | Cbo—D-But—CHA—Arg—pNA.HBr $C_{33}H_{47}N_8O_7Br$ | 1d (2 mmole) Cbo—D-But—OpNP (2.2 mmole) | (1e) 87.6 | C H N Br | 52.88 6.40 15.28 10.53 | 53.01 6.34 14.99 10.69 |
| 42e | Cbo—D-CHG—Tyr—Arg—pNA.HBr $C_{37}H_{47}N_8O_8Br$ | 42d (1 mmole) Cbo—D-CHG—OpNP (1.1 mmole) | (1e) 74.1 | C H N Br | 54.59 5.88 14.05 9.57 | 54.75 5.84 13.81 9.84 |
| 43e | Cbo—D-CHA—Tyr—Arg—pNA.HBr $C_{38}H_{49}N_8O_8Br$ | 42d (1 mmole) Cbo—D-CHA—OpNP (1.1 mmole) | (1e) 70.6 | C H N Br | 54.96 6.04 13.77 9.51 | 55.27 5.98 13.57 9.68 |
| 44e | Cbo—D-Nval—Tyr—Arg—pNA.HBr $C_{34}H_{43}N_8O_8Br$ | 42d (1 mmole) Cbo—D-Nval—OpNP (1.1 mmole) | (1e) 69.8 | C H N | 52.70 5.64 14.82 | 52.92 5.62 14.52 |

TABLE 3-continued

| Example | Tripeptide precursor | Starting products (mmole) | Method (Example) yield % | Elementary analysis | found % | calc. % |
|---|---|---|---|---|---|---|
| 45e | Cbo—D-CHT—Tyr—Arg—pNA.HBr $C_{38}H_{49}N_8O_9Br$ | 42d (1 mmole) Cbo—D-CHT—OpNP (1.1 mmole) | (1e) 67.8 | Br C H N | 10.12 54.18 5.93 13.29 | 10.35 54.22 5.87 13.31 |
| 46e | Cbo—D-Phe—Tyr—Arg—pNA.HBr $C_{38}H_{43}N_8O_8Br$ | 42d (1 mmole) Cbo—D-Phe—OpNP (1.1 mmole) | (1e) 70.5 | Br C H N | 9.35 55.38 5.34 13.88 | 9.49 55.68 5.29 13.67 |
| 47e | Cbo—D-Ph'Gly—Tyr—Arg—pNA.HBr $C_{37}H_{41}N_8O_8Br$ | 42d (1 mmole) Cbo—D-Ph'Gly—OpNP (1.1 mmole) | (1e) 74.0 | Br C H N | 9.60 54.96 5.19 14.11 | 9.75 55.16 5.13 13.91 |
| 48e | Cbo—D-CHG—Ala—Arg—pNA.HBr $C_{31}H_{43}N_8O_7Br$ | 48d (1.5 mmole) Cbo—D-CHG—OpNP (1.65 mmole) | (1e) 86.7 | Br C H N | 9.84 51.66 6.06 15.80 | 9.92 51.74 6.02 15.57 |
| 49e | Cbo—D-CHA—Ala—Arg—pNA.HBr $C_{32}H_{45}N_8O_7Br$ | 48d (1.5 mmole) Cbo—D-CHA—OpNP (1.65 mmole) | (1e) 88.4 | Br C H N | 10.96 52.09 6.22 15.55 | 11.10 52.39 6.18 15.27 |
| 50e | Cbo—D-Phe—Leu—Arg—pNA.HBr $C_{35}H_{45}N_8O_7Br$ | 11d (2 mmole) Cbo—D-Phe—OpNP (2.2 mmole) | (1e) 86.2 | Br C H N | 10.70 54.48 5.91 14.65 | 10.89 54.62 5.89 14.56 |
| 51e | Cbo—D-CHT—Leu—Arg—pNA.HBr $C_{35}H_{51}N_8O_8Br$ | 11d (2 mmole) Cbo—D-CHT—OpNP (2.2 mmole) | (1e) 79.4 | Br C H N | 10.22 52.78 6.51 14.30 | 10.38 53.09 6.49 14.15 |
| 52e | Cbo—D-CHA—Leu—Arg—pNA.HBr $C_{35}H_{51}N_8O_7Br$ | 11d (2 mmole) Cbo—D-CHA—OpNP (2.2 mmole) | (1e) 86.0 | Br C H N | 9.92 53.88 6.65 14.75 | 10.09 54.19 6.63 14.45 |
| 53e | Cbo—D-Leu—Ph'Gly—Arg—pNA.HBr $C_{34}H_{43}N_8O_7Br$ | 53d (1 mmole) Cbo—D-Leu—OpNP (1.1 mmole) | (1e) 79.5 | Br C H N | 10.18 53.80 5.76 15.08 | 10.30 54.04 5.74 14.83 |
| 54e | Cbo—D-Nval—Ph'Gly—Arg—pNA.HBr $C_{33}H_{41}N_8O_7Br$ | 53d (1 mmole) Cbo—D-Nval—OpNP (1.1 mmole) | (1e) 80.4 | Br C H N | 10.41 53.19 5.62 15.24 | 10.57 53.44 5.57 15.11 |
| 55e | Cbo—D-Ala—Ph'Gly—Arg—pNA.HBr $C_{31}H_{37}N_8O_7Br$ | 53d (1 mmole) Cbo—D-Ala—OpNP (1.1 mmole) | (1e) 81.6 | Br C H N | 10.65 52.00 5.29 15.95 | 10.77 52.18 5.23 15.70 |
| 56e | Cbo—D-CHA—Ph'Gly—Arg—pNA.HBr $C_{37}H_{47}N_8O_7Br$ | 53d (1 mmole) Cbo—D-CHA—OpNP (1.1 mmole) | (1e) 78.5 | Br C H N | 11.03 55.80 6.01 14.33 | 11.20 55.85 5.95 14.08 |
| 57e | Cbo—D-CHT—Ph'Gly—Arg—pNA.HBr $C_{37}H_{47}N_8O_8Br$ | 53d (1 mmole) Cbo—D-CHT—OpNP (1.1 mmole) | (1e) 74.6 | Br C H N | 9.88 54.85 5.90 14.08 | 10.04 54.75 5.84 13.81 |
| 58e | Cbo—D-CHG—Ph'Gly—Arg—pNA.HBr $C_{36}H_{45}N_8O_7Br$ | 53d (1 mmole) Cbo—D-CHG—OpNP (1.1 mmole) | (1e) 77.0 | Br C H N | 9.70 55.39 5.86 14.53 | 9.84 55.31 5.80 14.34 |
| 59e | Cbo—D-CHG—CHG—Arg—pNA.HBr $C_{36}H_{51}N_8O_7Br$ | 24d (1.5 mmole) Cbo—D-CHG—OpNP (1.65 mmole) | (1e) 82.6 | Br C H N | 10.08 54.99 6.60 14.41 | 10.22 54.89 6.53 14.23 |
| 60e | Cbo—D-Pip—CHG—Arg—pNA.HBr $C_{34}H_{47}N_8O_7Br$ | 24d (1.5 mmole) Cbo—D-Pip—OpNP (1.65 mmole) | (1e) 80.1 | Br C H N | 9.89 53.66 6.31 14.93 | 10.14 53.75 6.24 14.75 |
| 61e | Cbo—D-Phe—CHG—Arg—pNA.HBr $C_{37}H_{47}N_8O_7Br$ | 24d (1.5 mmole) Cbo—D-Phe—OpNP (1.65 mmole) | (1e) 88.7 | Br C H N | 10.42 55.78 6.01 14.22 | 10.52 55.85 5.95 14.08 |
| 62e | Cbo—D-Ph'Gly—CHG—Arg—pNA.HBr $C_{36}H_{45}N_8O_7Br$ | 24d (1.5 mmole) Cbo—D-Ph'Gly—OpNP (1.65 mmole) | (1e) 83.5 | Br C H N | 9.88 55.45 5.86 14.55 | 10.04 55.31 5.80 14.34 |
| 63e | Cbo—D-Ph'Gly—Phe—Arg—pNA.HBr $C_{37}H_{41}N_8O_7Br$ | 16d (1 mmole) Cbo—D-Ph'Gly—OpNP (1.1 mmole) | (1e) 86.0 | Br C H N | 10.09 56.18 5.24 14.33 | 10.22 56.27 5.23 14.19 |
| 64e | Cbo—D-CHA—Phe—Arg—pNA.HBr | 16d (1 mmole) | (1e) | Br C | 9.95 56.18 | 10.12 56.36 |

TABLE 3-continued

| Example | Tripeptide precursor | Starting products (mmole) | Method (Example) yield % | Elementary analysis | found % | calc. % |
|---|---|---|---|---|---|---|
| | C₃₈H₄₉N₈O₇Br | Cbo—D-CHA—OpNP (1.1 mmole) | 85.6 | H<br>N<br>Br | 6.12<br>14.01<br>9.81 | 6.10<br>13.84<br>9.87 |
| 65e | Cbo—D-CHG—Pip—Arg—pNA.HBr<br>C₃₄H₄₇N₈O₇Br | 28d (1 mmole)<br>Cbo—D-CHG—OpNP<br>(1.1 mmole) | (1e)<br>42.1 | C<br>H<br>N<br>Br | 53.53<br>6.27<br>14.95<br>10.39 | 53.75<br>6.24<br>14.75<br>10.52 |
| 66e | Cbo—D-CHA—Pip—Arg—pNA.HBr<br>C₃₅H₄₉N₈O₇Br | 28d (1 mmole)<br>Cbo—D-CHA—OpNP<br>(1.1 mmole) | (1e)<br>44.8 | C<br>H<br>N<br>Br | 54.17<br>6.41<br>14.62<br>10.13 | 54.33<br>6.38<br>14.48<br>10.33 |
| 67e | Cbo—D-CHG—Nleu—Arg—pNA.HBr<br>C₃₄H₄₉N₈O₇Br | 67d (2 mmole)<br>Cbo—D-CHG—OpNP<br>(2.2 mmole) | (1e)<br>86.7 | C<br>H<br>N<br>Br | 53.43<br>6.53<br>14.95<br>10.28 | 53.61<br>6.48<br>14.71<br>10.49 |
| 68e | Cbo—D-CHA—Nleu—Arg—pNA.HBr<br>C₃₅H₅₁N₈O₇Br | 67d (2 mmole)<br>Cbo—D-CHA—OpNP<br>(2.2 mmole) | (1e)<br>83.5 | C<br>H<br>N<br>Br | 53.88<br>6.71<br>14.59<br>10.21 | 54.19<br>6.63<br>14.45<br>10.30 |
| 69e | Cbo—D-CHA—Nval—Arg—pNA.HBr<br>C₃₄H₄₉N₈O₇Br | 69d (1 mmole)<br>Cbo—D-CHA—OpNP<br>(1.1 mmole) | (1e)<br>86.0 | C<br>H<br>N<br>Br | 53.48<br>6.46<br>14.80<br>10.31 | 53.61<br>6.48<br>14.71<br>10.49 |
| 70e | Cbo—D-CHG—Nval—Arg—pNA.HBr<br>C₃₃H₄₇N₈O₇Br | 69d (1 mmole)<br>Cbo—D-CHG—OpNP<br>(1.1 mmole) | (1e)<br>88.8 | C<br>H<br>N<br>Br | 52.88<br>6.35<br>15.18<br>10.49 | 53.01<br>6.34<br>14.99<br>10.69 |
| 71e | Cbo—D-Nval—CHA—Lys(ε-Cbo)—pNA<br>C₄₂H₅₄N₆O₉ | 14d (1.5 mmole)<br>Cbo—D-Nval—OpNP<br>(1.65 mmole) | (2e)<br>90.6 | C<br>H<br>N | 63.90<br>6.98<br>10.82 | 64.10<br>6.92<br>10.68 |
| 72e | Cbo—D-But—CHA—Lys(ε-Cbo)—pNA<br>C₄₁H₅₂N₆O₉ | 14d (1.5 mmole)<br>Cbo—D-But—OpNP<br>(1.65 mmole) | (2e)<br>91.4 | C<br>H<br>N | 63.48<br>6.82<br>10.99 | 63.71<br>6.78<br>10.87 |
| 73e | Cbo—D-Leu—CHA—Lys(ε-Cbo)—pNA<br>C₄₃H₅₆N₆O₉ | 14d (1.5 mmole)<br>Cbo—D-Leu—OpNP<br>(1.65 mmole) | (2e)<br>88.5 | C<br>H<br>N | 64.28<br>7.11<br>10.75 | 64.48<br>7.05<br>10.49 |
| 74e | Cbo—D-Nleu—CHA—Lys(ε-Cbo)—pNA<br>C₄₃H₅₆N₆O₉ | 14d (1.5 mmole)<br>Cbo—D-Nleu—OpNP<br>(1.65 mmole) | (2e)<br>88.9 | C<br>H<br>N | 64.18<br>7.08<br>10.60 | 64.48<br>7.05<br>10.49 |
| 75e | Cbo—D-CHG—But—Arg—pNA.HBr<br>C₃₂H₄₅N₈O₇Br | 75d (2 mmole)<br>Cbo—D-CHG—OpNP<br>(2.2 mmole) | (1e)<br>84.7 | C<br>H<br>N<br>Br | 52.19<br>6.17<br>15.35<br>10.70 | 52.39<br>6.18<br>15.27<br>10.89 |
| 76e | Cbo—D-CHA—But—Arg—pNA.HBr<br>C₃₃H₄₇N₈O₇Br | 75d (2 mmole)<br>Cbo—D-CHA—OpNP<br>(2.2 mmole) | (1e)<br>80.6 | C<br>H<br>N<br>Br | 52.87<br>6.41<br>15.17<br>10.55 | 53.01<br>6.34<br>14.99<br>10.69 |
| 77e | Cbo—D-CHT—But—Arg—pNA.HBr<br>C₃₃H₄₇N₈O₈Br | 75d (2 mmole)<br>Cbo—D-CHT—OpNP<br>(2.2 mmole) | (1e)<br>83.3 | C<br>H<br>N<br>Br | 51.72<br>6.25<br>14.88<br>10.37 | 51.90<br>6.20<br>14.67<br>10.46 |

EXAMPLE 78

2AcOH.H-D-Nval-CHA-Arg-pNA 7.09 g (10 mmoles) of 2HBr.H-D-Nval-CHA-Arg-pNA (prepared according to Example 38) were dissolved in 75 ml of 60% aqueous MeOH. The solution was charged on a column of "Amberlite" (Trademark) JRA-401 in the acetate form. The column was eluted with 60% aqueous MeOH whereby HBr was replaced by AcOH by ion exchange. The eluate was concentrated to dryness in vacuo at 40° C. After drying in the vacuum desiccator at 40° C. over $P_2O_5$ 6.33 g of bromide-free 2AcOH.H-D-Nval-CHA-Arg-pNA (98.5% of the theory) were obtained.

According to this method other salts with organic acids, e.g. formic acid, propionic acid, oxalic acid, tartaric acid, citric acid, lactic acid, benzoic acid, chlorobenzoic acid, salicylic acid or phthalic acid, can be prepared from the above mentioned tripeptide derivative. An ion exchanger, e.g. "Amberlite" JRA-401 in the hydrochloride form, can be used and converted into the desired acid salt form by converting the said ion exchanger into the basic OH-form by treatment with caustic soda solution and then treating the basic ion exchanger with a solution of a 1:1 mixture of the desired organic acid and its sodium salt in 60% aqueous MeOH.

The quantitative enzyme assays by means of the tripeptide substrates of the invention can be carried out as follows:

1. Assay of urine kallikrein:

1 ml of urine and 1 ml of TRIS-imidazole buffer having a pH of 7.9 and an ionic strength of 1.0 are incubated at 37° C. for 5 minutes and then centrifuged in order to remove sediments.

1.4 ml of distilled water heated to 37° C. and 0.4 ml of the centrifugate are well mixed in a plastic cuvette. To this mixture 0.2 ml. of a $2 \times 10^{-3}$ molar aqueous substrate solution is added, and the components are quickly mixed. This mixture is incubated for exactly 15 minutes at 37° C. The reaction mixture is then mixed with 0.2 ml of glacial acetic acid in order to stop the enzymatic reaction. For color measurement one uses a blank sample consisting of the same components but having the glacial acetic acid added thereto prior to the addition of the substrate in order to prevent the enzymatic reaction. Then, the quantity of the colored compound R—NH$_2$ formed is determined photometrically or spectrophotometrically at 405 nm from the difference between the blank sample and the test sample. From the obtained value the urine kallikrein activity in urine is determined according to the following formula:

$$\frac{\Delta OH_{15\ min.} \times V \times 1000 \times F}{15\ min. \times v \times \epsilon} = m\mu/ml\ of\ urine$$

$\Delta OD$ = increase of the optical density at 405 nm during 15 minutes
$V$ = total volume of the test mixture = 2.2 ml
1000 = conversion factor for converting U into mU
$F$ = dilution factor of urine (2)
$v$ = volume of the sample = 0.4 ml
$\epsilon$ = extinction coefficient divided by 1000 = 10.4

The calculation of the urine kallikrein content in urine can also be carried out by continuous measurement of the product R—NH$_2$ (e.g. p-nitroaniline) which is formed. This method is described hereinafter as applied to the assay of glandular kallikrein in sputum.

In addition to urine kallikrein urine also contains urokinase as a proteolytic enzyme which might also split the substrates of this invention, though to a minor extent. In the assay method described above the sum of the activities of urine kallikrein and urokinase is measured. In order to obtain the accurate value of the urine kallikrein activity, the urokinase activity has to be deducted. The latter can be determined in a comparative test by adding 0.075 unit of trypsin inhibitor (trypsin inhibitor from bovine lung) per ml of buffer in order to completely inhibit the urine kallikrein activity and measuring solely the urokinase activity.

2. Assay of glandular kallikrein in sputum:

0.5 ml of sputum is mixed with 2 ml of TRIS-imidazole buffer (ionic strength 1.0), and the mixture is pre-incubated at 37° C. for 5 minutes. The incubate is centrifuged. A test cuvette is charged with 1.5 ml of distilled water of 37° C., and 0.25 ml of the centrifugate is added. The components are well mixed. Then, 0.2 ml of a $2 \times 10^{-3}$ molar aqueous substrate solution is admixed. The change in the extinction at 405 nm is then followed continuously for 5 to 10 minutes by means of a recorder. From the determined value of $\Delta OD$ per minute the kallikrein activity per ml of sputum in mU is calculated by means of the following formula:

$$\frac{\Delta OD_{min.} \times V \times 100 \times F}{v \times \epsilon} = m\mu/ml\ of\ sputum$$

$F = 5$
$V = 1.95$
$v = 0.25$
1 U (unit) = enzyme quantity which is capable of splitting 1 $\mu$mole of substrate in 1 minute under optimum or otherwise defined conditions of pH, ionic strength, temperature and substrate concentration In pancreatic juice pancreatic kallikrein is present mainly in the form of prekallikrein and can be assayed only after activation, e.g. by means of trypsin. After activation of prekallikrein the trypsin is inhibited by means of soy bean trypsin inhibitor (SBTI). The kallikrein content in this activation mixture can be determined by one of the above described methods.

3. Assay of plasmin:

1.7 ml of TRIS-imidazole buffer (pH 7.5, ionic strength 0.2) is mixed with 0.1 ml of a solution of plasmin in 25% glycerol at 37° C., and the mixture is incubated at 37° C. for 1 minute. 0.2 ml of an aqueous $2 \times 10^{-3}$ molar substrate solution of 37° C. is added to the mixture, and the components are quickly mixed. The quantity of the split product R—NH$_2$ released from the substrate per time unit is then continuously measured. From the value determined per minute the plasmin activity per ml of sample in mU is calculated from the following formula:

$$\frac{\Delta E/min. \times V \times 1000}{v \times \epsilon} = m\mu/ml\ of\ sample$$

$\Delta E$ = quantity of split product released per minute
$V$ = total volume of test mixture
$v$ = volume of sample
$\epsilon$ = extinction coefficient divided by 1000

4. Assay of antiplasmin in human plasma:

0.1 ml of plasma diluted with TRIS-imidazole buffer in the ratio of 1:20 is mixed with 0.02 ml of a solution of 1.25 CU of human plasmin (preparation of the firm AB Kabi, Stockholm, Sweden) and 50 ATU of hirudine (preparation of the firm Pentapharm A. G., Basle, Switzerland) per ml in 25% glycerol. The mixture is incubated for 90 seconds at 37° C. The incubate is mixed with 1.7 ml of TRIS-imidazole buffer (pH 7.5, ionic strength 0.2) of 37° C. and then with 0.2 ml of a $2 \times 10^{-3}$ molar aqueous substrate solution. The quantity of the split product R—NH$_2$ released from the substrate per time unit is then measured continuously. From the determined value the residual plasmin activity is calculated in the above mentioned manner.

In a blank test the plasma is replaced by the corresponding quantity of buffer, but otherwise the test is carried out in the above described manner. The determined plasmin activity corresponds to the starting plasmin quantity. The anitplasmin activity is calculated from the difference between the plasmin activity determined in the blank test and the residual plasmin activity determined in the test using plasma according to the following formula:

$$\frac{(\Delta E_{blank\ sample} - \Delta E_{plasma\ sample})/min. \times V \times F \times 1000}{v \times \epsilon} =$$

$mI\mu/ml\ of\ plasma$ $F$ = dilution factor of plasma (20).

The substrates of the invention can also be used for assaying plasminogen in human plasma by converting the plasminogen present in the plasma by means of urokinase or streptokinase in a buffer system and determining the quantity of the formed plasmin by means of one of the substrates of the invention according to the above described plasmin assaying method. The quantity of plasminogen originally present in the plasma derives from the value determined for plasmin since on activation 1 molecule of plasmin is formed from 1 molecule of plasminogen.

In the following Table 4 the susceptibility of some of the substrates of the invention to organ or glandular kallikrein, plasmin and thrombin is indicated.

TABLE 4

Activity of urine kallikrein in 1 ml of human urine*, submandibularis kallikrein in 1 ml of sputum, human plasmin and human NIH thrombin, measured by means of the substrates of the invention at constant substrate and enzyme concentrations. For comparison (except thrombin) the corresponding values for the known commercially available substrates 2HCl.H—D-Val—Leu—Arg—pNA (A) and 2HCl.H—D-Val—Leu—Lys—pNA (B) (cf. German patent application OS 26 29 067) are also indicated. Substrate concentration: $2 \times 10^{-4}$ molar.

Quantity in nanomole of the split product R—NH$_2$ released in 1 minute by 1 ml of human urine, 1 ml of human sputum, 1 CU unit of human plasmin and 1 NIH unit of human thrombin, respectively

| | urine kallikrein | submandibularis kallikrein | human plasmin | human thrombin |
|---|---|---|---|---|
| A | 0.90 | 12.2 | 83 | |
| B | 0.30 | 5.7 | 347 | | substrates according to Example

| | urine kallikrein | submandibularis kallikrein | human plasmin | human thrombin |
|---|---|---|---|---|
| 1 | 0.84 | 12.9 | 699 | 8.27 |
| 2 | 0.80 | 25.6 | 1150 | |
| 3 | 2.55 | 31.2 | 430 | |
| 4 | 0.60 | 15.7 | 1120 | |
| 5 | 2.42 | 28.5 | 408 | |
| 6 | 0.72 | 24.8 | 1215 | |
| 7 | 2.55 | 31.1 | 428 | |
| 8 | 0.58 | 17.6 | 1180 | |
| 9 | 2.38 | 25.4 | 388 | |
| 10 | 0.61 | 14.9 | 1165 | |
| 11 | 0.60 | 11.6 | 381 | 33.9 |
| 12 | 2.75 | 30.5 | 421 | 4.0 |
| 13 | 2.67 | 36.6 | 446 | 7.44 |
| 14 | 1.02 | 6.7 | 505 | 0.35 |
| 15 | 2.50 | 23.1 | 440 | 0.39 |
| 16 | 3.31 | 32.2 | 1200 | 17.1 |
| 17 | 0.77 | 7.4 | 860 | 18.7 |
| 18 | 0.67 | 8.5 | 1200 | 4.53 |
| 19 | 1.40 | 8.1 | 1200 | 54.4 |
| 20 | 0.28 | 4.4 | 500 | 0.99 |
| 21 | 0.40 | 2.2 | 460 | 1.20 |
| 22 | 0.63 | 11.7 | 250 | 0.75 |
| 23 | 1.20 | 21.4 | 690 | 45.8 |
| 24 | 1.87 | 5.7 | 10 | 0.29 |
| 25 | 0.52 | 10.7 | 390 | 1.52 |
| 26 | 0.19 | 8.3 | 194 | 0.8 |
| 27 | 0.33 | 12.9 | 511 | 96.3 |
| 28 | 0 | 9.9 | 122 | 80.4 |
| 29 | 0.71 | 4.4 | 639 | 4.54 |
| 30 | 0 | 1.3 | 61 | 0.27 |
| 31 | 0 | 1.9 | 231 | 3.78 |
| 32 | 0.20 | 3.8 | 613 | 0.8 |
| 33 | 0.10 | 0.9 | 837 | 0.4 |
| 34 | 1.40 | 16.5 | 532 | 0.4 |
| 35 | 0.10 | 0.9 | 894 | 0.5 |
| 36 | 3.11 | 35.9 | 1069 | 6.8 |
| 37 | 2.08 | 28.1 | 1179 | 7.3 |
| 38 | 3.12 | 41.3 | 969 | 5.1 |
| 39 | 2.14 | 28.5 | 814 | 3.9 |
| 40 | 1.73 | 22.4 | 433 | 1.5 |
| 41 | 2.99 | 31.2 | 623 | 2.8 |
| 42 | 0.49 | 3.9 | 969 | 2.0 |
| 43 | 0.49 | 5.2 | 1407 | 8.3 |
| 44 | 0.42 | 4.9 | 1219 | 1.8 |
| 45 | 0.59 | 10.9 | 1252 | 9.5 |
| 46 | 0.26 | 6.1 | 843 | 2.6 |
| 47 | 0.19 | 7.0 | 818 | 1.0 |
| 48 | 0.72 | 9.5 | 239 | 158 |
| 49 | 0.66 | 10.6 | 389 | 163.5 |
| 50 | 0.61 | 6.8 | 313 | 14.4 |
| 51 | 0.33 | 11.7 | 596 | 58.1 |
| 52 | 0.64 | 8.8 | 555 | 57.6 |
| 53 | 0.67 | 25.8 | 422 | 27.4 |
| 54 | 0.58 | 22.9 | 382 | 19.2 |
| 55 | 0.42 | 23.5 | 141 | 4.2 |
| 56 | 0.64 | 29.4 | 559 | 120.2 |
| 57 | 0.45 | 31.1 | 591 | 112.1 |
| 58 | 0.38 | 22.1 | 446 | 63.7 |
| 59 | 0.33 | 5.9 | 101 | 7.5 |
| 60 | 0 | 1.4 | 10 | 1.3 |
| 61 | 0.33 | 4.9 | 60 | 3.7 |
| 62 | 0.25 | 7.2 | 26 | 2.4 |
| 63 | 0.42 | 7.0 | 841 | 2.4 |
| 64 | 0.5 | 9.7 | 1261 | 25.8 |
| 65 | 1.92 | 14.2 | 259 | 142.5 |
| 66 | 0.53 | 9.8 | 228 | 114.2 |
| 67 | 0.53 | 13.5 | 739 | 41.0 |
| 68 | 0.45 | 15.0 | 899 | 77.6 |
| 69 | 0.35 | 14.2 | 574 | 97.1 |
| 70 | 0.38 | 24.2 | 488 | 67.4 |
| 71 | 1.87 | 18.04 | 655 | 6.9 |
| 72 | 2.22 | 21.0 | 532 | 3.6 |
| 73 | 1.73 | 19.3 | 778 | 3.4 |
| 74 | 0.77 | 8.4 | 695 | 3.9 |
| 75 | 0.51 | 14.5 | 439 | 102.9 |
| 76 | 0.51 | 18.1 | 478 | 108.9 |
| 77 | 0.64 | 18.2 | 463 | 114.2 |

*Urine sample obtained by mixing 100 ml portions of morning urine of healthy persons.

The measurement of the split product R—NH$_2$ formed by the enzymatic hydrolysis of the substrate is based on the premise that the split product has an UV spectrum which differs from that of the substrate and is shifted towards higher wave lengths. The absorption of the substrate at 405 nm is practically nil. p-Nitroaniline as a split product shows an absorption maximum at 380 nm and a molar extinction coefficient of 13,200. At 405 nm the extinction coefficient is but slightly lower, i.e. 9650. The degree of the enzymatic hydrolysis of the substrate, which is proportional to the quantity of released p-nitroaniline, can be determined by spectrophotometric measurement at 405 nm. Even in the presence of excess substrate the measurement at 405 nm is not disturbed.

With the substrates containing a 2-naphthylamino-, 4-methoxy-2-naphthylamino, 4-methyl-coumaryl-(7)-amino or 1,3-di(methoxycarbonyl)-phenyl-(5)-amino group the quantity of the split product R—NH$_2$ is measured by fluorescence spectrophotometry. In a test system consisting of enzyme, buffer and substrate the emitted light of lower energy is continuously measured at 400–470 nm after the formed fluorescent split product has been excited by light of higher energy. The quantity of split product formed per time unit is a measure for the existing enzyme activity. As defined 1 μmole of split product per minute corresponds to 1 enzyme unit, based on a given substrate.

I claim:

1. Tripeptide derivatives of the general formula $$H-D-X-Y-Z-R \qquad I$$

wherein
(a)
X represents a cyclohexylglycyl, cyclohexylalanyl or cyclohexyltyrosyl group, and
Y represents an alanyl, α-aminobutyryl, valyl, norvalyl, leucyl, norleucyl, isoleucyl, prolyl or pipecolinoyl group, or
(b)
Y represents a phenylalanyl, phenylglycyl or tyrosyl group, and
X represents a cyclohexylglycyl, cyclohexylalanyl, cyclohexyltyrosyl, phenylalanyl or phenylglycyl group,
and wherein
Z represents an arginyl or lysyl group, and
R represents a chromogenic group which can be split off by enzymatic hydrolysis and which is capable of forming a colored or fluorescent compound, and salts thereof with acids.

2. Tripeptide derivatives as claimed in claim 1 wherein the dipeptide fragment attached to Arg or Lys is a CHG-Ala, CHG-But, CHG-Nval, CHG-Leu, CHG-Nleu, CHG-Pro, CHG-Pip, CHA-Ala, CHA-But, CHA-Nval, CHA-Leu, CHA-Nleu, CHA-Pro, CHA-Pip, CHT-But, CHT-Leu, CHT-Pro or CHT-Pip group, or a CHG-Phe, CHG-Ph'Gly, CHG-Tyr, CHA-Phe, CHA-Ph'Gly, CHA-Tyr, CHT-Phe, CHT-Ph'Gly, CHT-Tyr, Phe-Tyr, Ph'Gly-Phe or Ph'Gly-Tyr group, or an Ala-CHA, Ala-Ph'Gly, But-CHA, Val-CHG, Val-CHA, Val-CHT, Nval-CHA, Nval-Ph'Gly, Nval-Tyr, Leu-CHA, Leu-Ph'Gly, Nleu-CHA, Ile-CHA, Pro-CHG, Pro-CHA or Pro-CHT group, or a Phe-CHA, Phe-CHG, Ph'Gly-CHA, Ph'Gly-CHG, Ph'Gly-CHT, CHG-CHA or CHG-CHG group.

3. Tripeptide derivatives as claimed in one of claims 1 or 2 wherein R is a p-nitrophenylamino, 2-naphthylamino, 4-methoxy-2-naphthylamino, 4-methyl-coumaryl-(7)-amino, 1,3-di(methoxycarbonyl)-phenyl-(5)-amino, quinonylamino or nitroquinonylamino group.

4. Tripeptide derivatives as claimed in one of claims 1 or 2 which are protonated with a mineral acid, e.g. HCl, HBr, $H_2SO_4$ or $H_3PO_4$, or an organic acid, e.g. formic acid, acetic acid, propionic acid, trimethylacetic acid, methoxyacetic acid, halogenated acetic acids such as trichloro- or trifluoroacetic acids, aminoacetic acid, lactic acid, oxalic acid, malonic acid, citric acid, benzoic acid, aromatic acids substituted in the nucleus such as toluic acids, chloro- or bromobenzoic acids, methoxybenzoic acids and aminobenzoic acids, or phthalic acid.

5. Tripeptide derivatives as claimed in claim 2 wherein R is a p-nitrophenylamino, 2-naphthylamino, 4-methoxy-2-naphthylamino, 4-methyl-coumaryl-(7)-amino, 1,3-di(methoxycarbonyl)-phenyl-(5)-amino, quinonylamino or nitro-quinonylamino group.

6. Tripeptide derivatives as claimed in claim 2 which are protonated with a mineral acid, e.g. HCl, HBr, $H_2SO_4$ or $H_3PO_4$, or an organic acid, e.g. formic acid, acetic acid, propionic acid, trimethylacetic acid, methoxyacetic acid, halogenated acetic acids such as trichloro- or trifluoroacetic acids, aminoacetic acid, lactic acid, oxalic acid, malonic acid, citric acid, benzoic acid, aromatic acids substituted in the nucleus such as toluic acids, chloro- or bromobenzoic acids, methoxybenzoic acids and aminobenzoic acids, or phthalic acid.

* * * * *

UNITED STATES PATENT AND TRADEMARK OFFICE
CERTIFICATE OF CORRECTION

PATENT NO. : 4,428,874

DATED : January 31, 1984

INVENTOR(S) : L.G. Svendsen

It is certified that error appears in the above-identified patent and that said Letters Patent is hereby corrected as shown below:

Claim 1 should appear as shown below:

1. Tripeptide derivatives of the general formula $$H-D-X-Y-Z-R$$

wherein
    (a) X represents a cyclohexylglycyl, cyclohexylalanyl or cyclohexyltyrosyl group, and
    Y represents an alanyl, $\alpha$-aminobutyryl, valyl, norvalyl, leucyl, norleucyl, isoleucyl, prolyl or pipecolinoyl group, or
    (b) Y represents a phenylalanyl, phenylglycyl or tyrosyl group, and
    X represents a cyclohexylglycyl, cyclohexylalanyl, cyclohexyltyrosyl, phenylalanyl or phenylglycyl group, or
    (c) Y represents a cyclohexyglycyl, cyclohexylalanyl, cyclohexyltyrosyl, phenylglycyl or tyrosyl group, and

UNITED STATES PATENT AND TRADEMARK OFFICE
CERTIFICATE OF CORRECTION

PATENT NO. : 4,428,874

DATED : January 31, 1984

INVENTOR(S) : L.G. Svendsen

It is certified that error appears in the above-identified patent and that said Letters Patent is hereby corrected as shown below:

> X represents an alanyl, α aminobutyryl, valyl, norvalyl, leucyl, norleucyl, isoleucyl or prolyl group, or
> (d) X represents a phenylalanyl, phenylglycycl or cyclohexylglycyl group and
> Y represents a cyclohexylalanyl, cyclohexylglycyl or cyclohexyltyrosyl group,
> and wherein
> Z represents an arginyl or lysyl group, and
> R represents a chromogenic group which can be split off by enzymatic hydrolysis and which is capable of forming a colored or fluorescent compound, and salts thereof with acids.

Signed and Sealed this

Seventeenth Day of September 1985

[SEAL]

Attest:

DONALD J. QUIGG

Attesting Officer

Commissioner of Patents and Trademarks—Designate